United States Patent
Zeng et al.

(10) Patent No.: US 12,128,125 B2
(45) Date of Patent: *Oct. 29, 2024

(54) POLYMER BLEND

(71) Applicants: Dow Global Technologies LLC, Midland, MI (US); Rohm and Haas Company, Collegeville, PA (US); Dow Silicones Corporation, Midland, MI (US)

(72) Inventors: Fanwen Zeng, Audubon, PA (US); Hilda G. Buss, Norristown, PA (US); Matthew Jeletic, Midland, MI (US); Xiaodong Lu, North Wales, PA (US); Tian Lan, Langhorne, PA (US); Isabelle Van Reeth, Incourt Walloon Brabant (BE); Helene Dihang, Taisnières-sur-Hon (FR); Marc Eeman, Sombreffe (BE); Bryan L. McCulloch, Olympia, WA (US); Jodi Mecca, Midland, MI (US); Ralph C. Even, Blue Bell, PA (US); Inna Shulman, Langhorne, PA (US); Michaeleen L. Pacholski, Collegeville, PA (US)

(73) Assignees: Dow Global Technologies LLC, Midland, MI (US); Rohm and Haas Company, Collegeville, PA (US); Dow Silicones Corporation, Midland, MI (US)

(*) Notice: Subject to any disclaimer, the term of this patent is extended or adjusted under 35 U.S.C. 154(b) by 799 days.

This patent is subject to a terminal disclaimer.

(21) Appl. No.: 17/287,394

(22) PCT Filed: Dec. 3, 2019

(86) PCT No.: PCT/US2019/064157
§ 371 (c)(1),
(2) Date: Apr. 21, 2021

(87) PCT Pub. No.: WO2020/123197
PCT Pub. Date: Jun. 18, 2020

(65) Prior Publication Data
US 2021/0401725 A1 Dec. 30, 2021

Related U.S. Application Data

(60) Provisional application No. 62/778,531, filed on Dec. 12, 2018.

(51) Int. Cl.
| | | |
|---|---|---|
| A61K 8/35 | (2006.01) | |
| A61K 8/34 | (2006.01) | |
| A61K 8/37 | (2006.01) | |
| A61K 8/40 | (2006.01) | |
| A61K 8/81 | (2006.01) | |
| A61K 8/895 | (2006.01) | |
| A61Q 17/04 | (2006.01) | |

(52) U.S. Cl.
CPC .............. *A61K 8/895* (2013.01); *A61K 8/345* (2013.01); *A61K 8/35* (2013.01); *A61K 8/37* (2013.01); *A61K 8/40* (2013.01); *A61K 8/8147* (2013.01); *A61Q 17/04* (2013.01); *A61K 2800/544* (2013.01)

(58) Field of Classification Search
CPC .......... A61K 8/895; A61K 8/345; A61K 8/35; A61K 8/37; A61K 8/40; A61K 8/8147; A61K 8/893; A61K 2800/544; A61Q 17/04; C08F 230/085; C08F 220/06; C08F 220/14; C08F 265/06; C08F 265/04; C08L 43/04; C08L 51/003
USPC .......................................................... 424/60
See application file for complete search history.

(56) References Cited

U.S. PATENT DOCUMENTS

| | | | |
|---|---|---|---|
| 6,060,072 A | 5/2000 | Konik et al. | |
| 6,534,590 B1 | 3/2003 | Aso et al. | |
| 9,351,916 B2 | 5/2016 | Li et al. | |
| 11,976,144 B2* | 5/2024 | Buss | C08F 220/06 |
| 2009/0186982 A1 | 7/2009 | Minge et al. | |
| 2014/0336343 A1 | 11/2014 | Yang | |
| 2015/0051438 A1 | 2/2015 | Taskin et al. | |
| 2015/0216787 A1 | 8/2015 | Hori et al. | |

(Continued)

FOREIGN PATENT DOCUMENTS

| | | |
|---|---|---|
| CN | 102918103 | 2/2013 |
| EP | 2181700 | 5/2010 |

(Continued)

OTHER PUBLICATIONS

Office Action from corresponding Brazilian Application No. BR112021009058 dated Jun. 23, 2023.

(Continued)

*Primary Examiner* — Hannah J Pak
(74) *Attorney, Agent, or Firm* — Thomas S. Deibert

(57) ABSTRACT

A polymer blend is provided comprising: (A) multistage polymer, comprising: acrylate rich stage comprising: structural units of monoethylenically unsaturated non-ionic, acrylate rich stage monomer selected from $C_{1-22}$ alkyl (meth) acrylates and mixtures thereof; and carbosiloxane rich stage, comprising: structural units of carbosiloxane monomer of formula (I); and (B) silicone-grafted vinyl copolymer, wherein the silicone-grafted vinyl copolymer, comprises: structural units of a vinyl (B) monomer; and structural units of a carbosiloxane dendrimer of formula (V). Also provided are personal care formulations comprising the polymer blend.

10 Claims, No Drawings

(56) References Cited

U.S. PATENT DOCUMENTS

| | | | |
|---|---|---|---|
| 2015/0232601 A1 | 8/2015 | Furukawa et al. | |
| 2016/0144089 A1 | 5/2016 | Woo et al. | |
| 2016/0355698 A1 | 12/2016 | Harris et al. | |
| 2018/0333345 A1 | 11/2018 | Tallon et al. | |
| 2021/0353524 A1* | 11/2021 | Zeng | A61Q 1/02 |
| 2024/0122840 A1* | 4/2024 | Lan | A61K 8/8152 |
| 2024/0124630 A1* | 4/2024 | Lan | A61K 8/8152 |

FOREIGN PATENT DOCUMENTS

| | | |
|---|---|---|
| EP | 3360536 | 8/2018 |
| WO | 2010026534 | 3/2010 |

OTHER PUBLICATIONS

Search Report from Chinese Application No. 201980077272.2 dated Sep. 14, 2023.

* cited by examiner

POLYMER BLEND

The present invention relates to a polymer blend. In particular, the present invention relates to a polymer blend comprising: (A) multistage polymer, comprising: acrylate rich stage comprising: structural units of monoethylenically unsaturated non-ionic, acrylate rich stage monomer selected from $C_{1-22}$ alkyl (meth)acrylates and mixtures thereof; and carbosiloxane rich stage, comprising: structural units of carbosiloxane monomer of formula (I); and (B) silicone-grafted vinyl copolymer, wherein the silicone-grafted vinyl copolymer, comprises: structural units of a vinyl (B) monomer; and structural units of a carbosiloxane dendrimer of formula (V).

Consumers desire personal care formulations that provide long wear properties, such that the formulation might be applied once and last through the work day and beyond without the need for refreshing or touching up. Given todays active lifestyles, it is no simple task to provide such long wear personal care formulations.

In addition, the damaging effects of sunlight on human skin are well documented. Six percent of the solar energy reaching the Earth's surface is ultraviolet (UV) radiation having a wavelength of 290 to 400 nm. This radiation is divided into two components: (i) low energy UVA radiation having a wavelength of 320 to 400 nm and (ii) high energy UVB radiation having a wavelength of 290 to 320 nm. While the UV portion of solar energy is relatively small, it induces nearly 99% of all the side effects from sunlight exposure. High energy UVB radiation, for example, is responsible for producing sunburn, appearance of skin aging and skin cancer. Low energy UVA radiation, for example, is responsible for inducing direct tanning and erythema (abnormal redness) of the skin and contributes to the appearance of skin aging.

By avoiding direct exposure to sunlight, individuals can avoid the serious effects caused by exposure to UV radiation. However, because of the nature of their work, it is challenging for some people to avoid such exposure. In addition, some people voluntarily expose their skin to the sun, e.g., to tan. Therefore, protection against the harmful effects of the sun is important.

Protection from the harmful effects of UV radiation exposure is available in the form of both topically applied formulations containing at least one physical UV blocker, or at least one chemical UV absorber, or combinations thereof. Physical blockers include active ingredients such as, titanium dioxide, zinc oxide and red petrolatum. Chemical absorbers include active ingredients, such as, paraaminobenzoic acid (more commonly known as PABA), which are generally transparent when applied and act by absorbing UV radiation, offering selective protection against certain UV wave bands, depending on the absorption spectrum of the active ingredient in the formulation.

The effectiveness of a given personal care formulation is assessed by how well it protects the skin in terms of a Sun Protection Factor (SPF) which is defined as the ratio of the amount of energy required to produce a minimal erythema on sunscreen protected skin to the amount of energy required to produce the same level of erythema on unprotected skin.

Some of the chemical absorbers and physical blockers (e.g., suncare actives) typically used in sunscreen formulations reportedly have adverse toxicological effects and negative sensory effects, which discourage people from using sunscreens. Therefore, it is desirable to reduce the level of suncare actives present in sunscreen formulations without reducing the SPF protection. Accordingly, a variety of SPF boosters have been developed for use in suncare formulations to reduce the level of suncare actives without a reduction in the SPF protection provided. It is also desirable that personal care formulations exhibit water resistance and retention of the suncare active ingredients in personal care formulations during use.

An approach to providing long wear formulations is disclosed by Konik et al. in U.S. Pat. No. 6,060,072. In U.S. Pat. No. 6,060,072, Konik et al. disclose water proof or water resistant cosmetic compositions which comprise a styrene-ethylene-propylene copolymer in an amount of 5 to 10%, a combination of a PVP/eicosene copolymer and tricontanyl PVP copolymer in an amount of 0.1 to 50%, a $C_{8-9}$ isoparaffin, a $C_{9-12}$ aliphatic hydrocarbon, or a combination thereof, in an amount of 50 to 85%.

Notwithstanding, there remains a need for new ingredients for use in personal care formulations that provide long wear properties and offer an effective SPF rating while reducing the necessary incorporation level of UV absorbing agents and exhibit water resistance and suncare active retention.

The present invention provides a polymer blend, comprising: (A) a multistage polymer, comprising: (a) an acrylate rich stage comprising: 88 to 100 wt %, based on weight of the acrylate rich stage, of structural units of a monoethylenically unsaturated non-ionic, acrylate rich stage monomer, wherein the monoethylenically unsaturated non-ionic, acrylate rich stage monomer is selected from the group consisting of $C_{1-22}$ alkyl (meth)acrylates and mixtures thereof; 0 to 10 wt %, based on weight of the acrylate rich stage, of structural units of a monoethylenically unsaturated carboxylic acid, acrylate rich stage monomer; and 0 to 2 wt %, based on weight of the acrylate rich stage, of structural units of a multiethylenically unsaturated, acrylate rich stage monomer having at least two ethylenically unsaturated groups per molecule; and (b) a carbosiloxane rich stage, comprising: 0 to 90 wt %, based on weight of the carbosiloxane rich stage, of structural units of a vinyl (A) monomer; and 10 to 100 wt %, based on weight of the carbosiloxane rich stage, of structural units of a carbosiloxane monomer of formula (I)

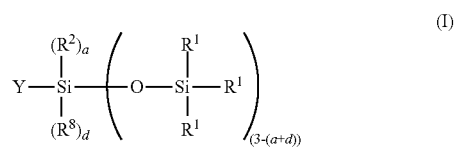

wherein a is 0 to 3; wherein d is 0 or 1; wherein each $R^1$ is independently selected from the group consisting of a hydrogen, a $C_{1-10}$ alkyl group and an aryl group; wherein each $R^2$ is independently selected from the group consisting of a hydrogen and a $C_{1-10}$ alkyl group; wherein each $R^8$ is a —O—Si(CH$_3$)$_2$—O—Si(CH$_3$)$_3$ group; wherein Y is selected from the group consisting of formula (II), (III) and (IV)

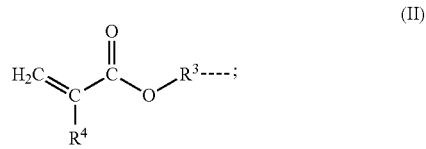

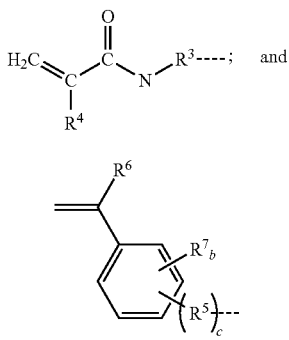
(III)

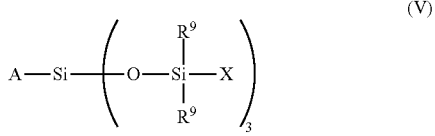
(IV)

wherein each $R^4$ and $R^6$ are independently selected from the group consisting of a hydrogen and a methyl group; wherein each $R^3$ and $R^5$ are independently a $C_{1-10}$ alkylene group; wherein each $R^7$ is independently a $C_{1-10}$ alkyl group; wherein b is 0 to 4 and wherein c is 0 or 1; and (B) a silicone-grafted vinyl copolymer, wherein the silicone-grafted vinyl copolymer, comprises: 25 to 95 wt %, based on weight of the silicone-grafted vinyl copolymer, of structural units of a vinyl (B) monomer; and 5 to 75 wt %, based on weight of the silicone-grafted vinyl copolymer, of structural units of a carbosiloxane dendrimer of formula (V)

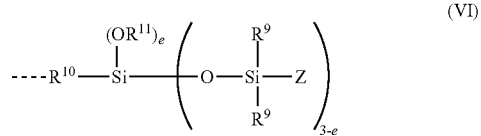
(V)

wherein each $R^9$ is independently selected from the group consisting of a $C_{1-10}$ alkyl group and an aryl group; wherein each X is a silylalkyl group of formula (VI)

(VI)

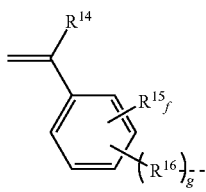

wherein $R^{19}$ is a $C_{2-10}$ alkylene group; wherein each $R^{11}$ is independently a $C_{1-10}$ alkyl group; wherein each Z is independently selected from the group consisting of a hydrogen, a $C_{1-10}$ alkyl group, an aryl group and a silylalkyl group of formula (VI); wherein e is 0 to 3; wherein A is selected from the group consisting of formula (VII), (VIII) and (IX)

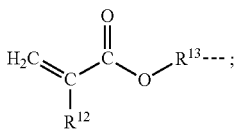
(VII)

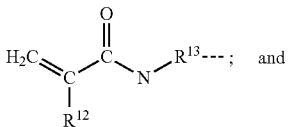
(VIII)

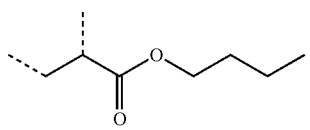
(IX)

wherein each $R^{12}$ and $R^{14}$ are independently a hydrogen or a methyl group; wherein each $R^{13}$ and $R^{16}$ are independently a $C_{1-10}$ alkylene group; wherein each $R^{15}$ is independently a $C_{1-10}$ alkyl group; wherein f is 0 to 4 and wherein g is 0 or 1.

The present invention provides a personal care formulation, comprising: a polymer blend of the present invention dispersed in a cosmetically acceptable carrier.

The present invention provides a method of treating the skin or hair of a mammal, comprising: providing a personal care formulation of the present invention, applying the personal care formulation to the skin or hair of a mammal.

DETAILED DESCRIPTION

We have identified a unique polymer blend of a multistage polymer and a silicone-grafted vinyl copolymer having desirable properties for use in personal care formulations, in particular for use in suncare formulations.

Unless otherwise indicated, ratios, percentages, parts, and the like are by weight.

The term "aesthetic characteristics" as used herein and in the appended claims in reference to a personal care formulation refers to visual and tactile sensory properties (e.g., smoothness, tack, lubricity, texture, color, clarity, turbidity, uniformity).

The term "structural units" as used herein and in the appended claims refers to the remnant of the indicated monomer in the claimed polymer; thus a structural unit of n-butyl acrylate is illustrated:

where the dotted lines represent the points of attachment to the polymer backbone.

The term "(meth)acrylic acid" as used herein and in the appended claims is intended to serve as a generic expression embracing both acrylic acid and methacrylic acid.

The term "(meth)acrylate" as used herein and in the appended claims is intended to serve as a generic expression embracing both acrylate and methacrylate.

The term "cosmetically acceptable" as used herein and in the appended refers to ingredients that are typically used for topical application to the skin, and is intended to underscore that materials that are toxic when present in the amounts typically found in skin care compositions are not contemplated as part of the present invention.

Preferably, the polymer blend of the present invention, comprises: (A) (preferably, 10 to 99 wt % (more preferably, 15 to 90 wt %; still more preferably, 20 to 80 wt %; most preferably, 25 to 75 wt %), based on weight solids of the polymer blend, of) a multistage polymer, comprising: (a) (preferably, 60 to 95 wt % (more preferably, 65 to 90 wt %; still more preferably, 70 to 85 wt %; most preferably, 75 to 82 wt %), based on weight of the multistage polymer, of) an acrylate rich stage comprising: 88 to 100 wt % (preferably, 94 to 99.49 wt %; more preferably, 97 to 99.23 wt %; still more preferably, 97.9 to 98.95 wt %; most preferably, 97.45 to 98.05 wt %), based on weight of the acrylate rich stage, of structural units of a monoethylenically unsaturated non-ionic, acrylate rich stage monomer, wherein the monoethylenically unsaturated non-ionic, acrylate rich stage monomer is selected from the group consisting of $C_{1-22}$ alkyl (meth)acrylates and mixtures thereof; 0 to 10 wt % (preferably, 0.5 to 5 wt %; more preferably, 0.75 to 2.5 wt %; still more preferably, 1 to 2 wt %; most preferably, 1.25 to 1.75 wt %), based on weight of the acrylate rich stage, of structural units of a monoethylenically unsaturated carboxylic acid, acrylate rich stage monomer; and 0 to 2 wt % (preferably, 0.01 to 1 wt %; more preferably, 0.02 to 0.5 wt %; still more preferably, 0.05 to 0.1 wt %; most preferably, 0.07 to 0.08 wt %), based on weight of the acrylate rich stage, of structural units of a multiethylenically unsaturated, acrylate rich stage monomer having at least two ethylenically unsaturated groups per molecule; and (b) (preferably, 5 to 40 wt % (more preferably, 10 to 35 wt %; still more preferably, 15 to 30 wt %; most preferably, 18 to 25 wt %), based on weight of the multistage polymer, of) a carbosiloxane rich stage, comprising: 0 to 90 wt % (preferably, 10 to 50 wt %; more preferably, 12.5 to 30 wt %; still more preferably, 15 to 25 wt %; most preferably, 19 to 21 wt %), based on weight of the carbosiloxane rich stage, of structural units of a vinyl (A) monomer; and 10 to 100 wt % (preferably, 50 to 90 wt %; more preferably, 70 to 87.5 wt %; still more preferably, 75 to 85 wt %; most preferably, 79 to 81 wt %), based on weight of the carbosiloxane rich stage, of structural units of a carbosiloxane monomer of formula (I)

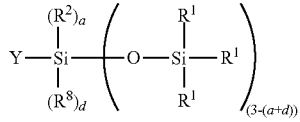
(I)

wherein a is 0 to 3; wherein d is 0 or 1; wherein each $R^1$ is independently selected from the group consisting of a hydrogen, a $C_{1-10}$ alkyl group and an aryl group; wherein each $R^2$ is independently selected from the group consisting of a hydrogen and a $C_{1-10}$ alkyl group; wherein each $R^8$ is a —O—Si(CH$_3$)$_2$—O—Si(CH$_3$)$_3$ group; wherein Y is selected from the group consisting of formula (II), (III) and (IV)

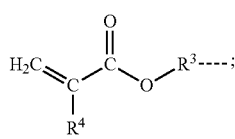
(II)

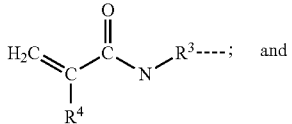
(III)

and

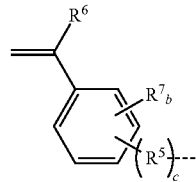
(IV)

wherein each $R^4$ and $R^6$ are independently selected from the group consisting of a hydrogen and a methyl group; wherein each $R^3$ and $R^5$ are independently a $C_{1-10}$ alkylene group; wherein each $R^7$ is independently a $C_{1-10}$ alkyl group; wherein b is 0 to 4 and wherein c is 0 or 1; and (B) (preferably, 1 to 90 wt % (preferably, 10 to 85 wt %; more preferably, 20 to 80 wt %; most preferably, 25 to 75 wt %), based on weight solids of the polymer blend, of) a silicone-grafted vinyl copolymer, wherein the silicone-grafted vinyl copolymer, comprises: 25 to 95 wt % (preferably, 30 to 70 wt %; more preferably, 40 to 60 wt %; still more preferably, 45 to 55 wt %; most preferably, 47.5 to 52.5 wt %), based on weight of the silicone-grafted vinyl copolymer, of structural units of a vinyl (B) monomer; and 5 to 75 wt % (preferably, 30 to 70 wt %; more preferably, 40 to 60 wt %; still more preferably, 45 to 55 wt %; most preferably, 47.5 to 52.5 wt %), based on weight of the silicone-grafted vinyl copolymer, of structural units of a carbosiloxane dendrimer of formula (V)

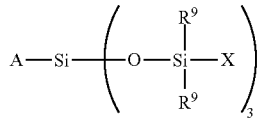
(V)

wherein each $R^9$ is independently selected from the group consisting of a $C_{1-10}$ alkyl group and an aryl group; wherein each X is a silylalkyl group of formula (VI)

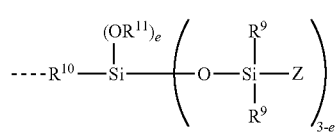
(VI)

wherein $R^{10}$ is a $C_{2-10}$ alkylene group; wherein each $R^{11}$ is independently a $C_{1-10}$ alkyl group; wherein each Z is independently selected from the group consisting of a hydrogen, a $C_{1-10}$ alkyl group, an aryl group and a silylalkyl group of formula (VI); wherein e is 0 to 3; wherein A is selected from the group consisting of formula (VII), (VIII) and (IX)

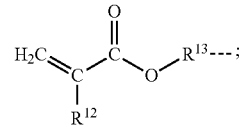
(VII)

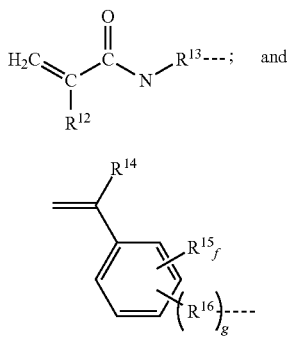

(VIII)

and (IX)

wherein each $R^{12}$ and $R^{14}$ are independently a hydrogen or a methyl group; wherein each $R^{13}$ and $R^{16}$ are independently a $C_{1-10}$ alkylene group; wherein each $R^{15}$ is independently a $C_{1-10}$ alkyl group; wherein f is 0 to 4 and wherein g is 0 or 1.

Preferably, the multistage polymer comprises an acrylate rich stage. More preferably, the multistage polymer, comprises: 60 to 95 wt % (preferably, 65 to 90 wt %; more preferably, 70 to 85 wt %; most preferably, 75 to 82 wt %), based on weight of the multistage polymer, of an acrylate rich stage. Most preferably, the multistage polymer, comprises 60 to 95 wt % (preferably, 65 to 90 wt %; more preferably, 70 to 85 wt %; most preferably, 75 to 82 wt %), based on weight of the multistage polymer, of an acrylate rich stage; wherein the acrylate rich stage, comprises: 88 to 100 wt % (preferably, 94 to 99.49 wt %; more preferably, 97 to 99.23 wt %; still more preferably, 97.9 to 98.95 wt %; most preferably, 97.45 to 98.05 wt %), based on weight of the acrylate rich stage, of structural units of a monoethylenically unsaturated non-ionic, acrylate rich stage monomer; wherein the monoethylenically unsaturated non-ionic, acrylate rich stage monomer is selected from the group consisting of $C_{1-22}$ alkyl (meth)acrylates and mixtures thereof; 0 to 10 wt % (preferably, 0.5 to 5 wt %; more preferably, 0.75 to 2.5 wt %; still more preferably, 1 to 2 wt %; most preferably, 1.25 to 1.75 wt %), based on weight of the acrylate rich stage, of structural units of a monoethylenically unsaturated carboxylic acid, acrylate rich stage monomer; and 0 to 2 wt % (preferably, 0.01 to 1 wt %; more preferably, 0.02 to 0.5 wt %; still more preferably, 0.05 to 0.1 wt %; most preferably, 0.07 to 0.08 wt %), based on weight of the acrylate rich stage, of structural units of a multiethylenically unsaturated, acrylate rich stage monomer having at least two ethylenically unsaturated groups per molecule.

Preferably, the acrylate rich stage comprises: 88 to 100 wt % (preferably, 94 to 99.49 wt %; more preferably, 97 to 99.23 wt %; still more preferably, 97.9 to 98.95 wt %; most preferably, 97.45 to 98.05 wt %), based on weight of the acrylate rich stage, of structural units of a monoethylenically unsaturated non-ionic, acrylate rich stage monomer; wherein the monoethylenically unsaturated non-ionic, acrylate rich stage monomer is selected from the group consisting of $C_{1-22}$ alkyl (meth)acrylates and mixtures thereof. More preferably, the acrylate rich stage comprises: 88 to 100 wt % (preferably, 94 to 99.49 wt %; more preferably, 97 to 99.23 wt %; still more preferably, 97.9 to 98.95 wt %; most preferably, 97.45 to 98.05 wt %), based on weight of the acrylate rich stage, of structural units of a monoethylenically unsaturated non-ionic, acrylate rich stage monomer, wherein the monoethylenically unsaturated non-ionic, acrylate rich stage monomer is selected from the group consisting of a mixture of at least two $C_{1-12}$ alkyl (meth)acrylates. Still more preferably, the acrylate rich stage comprises: 88 to 100 wt % (preferably, 94 to 99.49 wt %; more preferably, 97 to 99.23 wt %; still more preferably, 97.9 to 98.95 wt %; most preferably, 97.45 to 98.05 wt %), based on weight of the acrylate rich stage, of structural units of a monoethylenically unsaturated non-ionic, acrylate rich stage monomer, wherein the monoethylenically unsaturated non-ionic, acrylate rich stage monomer is selected from the group consisting of a mixture of at least two $C_{1-8}$ alkyl (meth)acrylates. Yet more preferably, the acrylate rich stage comprises: 88 to 100 wt % (preferably, 94 to 99.49 wt %; more preferably, 97 to 99.23 wt %; still more preferably, 97.9 to 98.95 wt %; most preferably, 97.45 to 98.05 wt %), based on weight of the acrylate rich stage, of structural units of a monoethylenically unsaturated non-ionic, acrylate rich stage monomer, wherein the monoethylenically unsaturated non-ionic, acrylate rich stage monomer is selected from the group consisting of a mixture of at least three $C_{1-8}$ alkyl (meth)acrylates.

Preferably, the acrylate rich stage comprises: 88 to 100 wt % (preferably, 94 to 99.49 wt %; more preferably, 97 to 99.23 wt %; still more preferably, 97.9 to 98.95 wt %; most preferably, 97.45 to 98.05 wt %), based on weight of the acrylate rich stage, of structural units of a monoethylenically unsaturated non-ionic, acrylate rich stage monomer; wherein the monoethylenically unsaturated non-ionic, acrylate rich stage monomer is selected from the group consisting of a mixture of (i) 40 to 75 wt % (more preferably, 50 to 70 wt %; most preferably, 55 to 65 wt %), based on weight of the acrylate rich stage, of at least one $C_{1-5}$ alkyl (meth)acrylate and (ii) 25 to 60 wt % (more preferably, 30 to 50 wt %; most preferably, 35 to 45 wt %), based on weight of the acrylate rich stage, of at least one $C_{6-22}$ alkyl (meth)acrylate. More preferably, the acrylate rich stage comprises: 88 to 100 wt % (preferably, 94 to 99.49 wt %; more preferably, 97 to 99.23 wt %; still more preferably, 97.9 to 98.95 wt %; most preferably, 97.45 to 98.05 wt %), based on weight of the acrylate rich stage, of structural units of a monoethylenically unsaturated non-ionic, acrylate rich stage monomer; wherein the monoethylenically unsaturated non-ionic, acrylate rich stage monomer is selected from the group consisting of a mixture of (i) 40 to 75 wt % (more preferably, 50 to 70 wt %; most preferably, 55 to 65 wt %), based on weight of the acrylate rich stage, of at least one $C_{1-4}$ alkyl (meth)acrylate selected from the group consisting of butyl (meth)acrylate, isobutyl (meth)acrylate, methyl (meth)acrylate and mixtures thereof; and (ii) 25 to 60 wt % (more preferably, 30 to 50 wt %; most preferably, 35 to 45 wt %), based on weight of the acrylate rich stage, of at least one $C_{6-22}$ alkyl (meth)acrylate selected from the group consisting of ethylhexyl (meth)acrylate, lauryl (meth)acrylate, stearyl (meth)acrylate, cetyl-eicosyl (meth)acrylate, behenyl (meth)acrylate and mixtures thereof. Still more preferably, the acrylate rich stage comprises: 88 to 100 wt % (preferably, 94 to 99.49 wt %; more preferably, 97 to 99.23 wt %; still more preferably, 97.9 to 98.95 wt %; most preferably, 97.45 to 98.05 wt %), based on weight of the acrylate rich stage, of structural units of a monoethylenically unsaturated non-ionic, acrylate rich stage monomer; wherein the monoethylenically unsaturated non-ionic, acrylate rich stage monomer is selected from the group consisting of a mixture of (i) 40 to 75 wt % (more preferably, 50 to 70 wt %; most preferably, 55 to 65 wt %), based on weight of the acrylate rich stage, of at least one $C_{1-4}$ alkyl (meth)acrylate selected from the group consisting of butyl acrylate, butyl methacrylate isobutyl methacrylate, methyl methacrylate and mixtures thereof; and (ii) 25 to 60 wt % (more preferably, 30 to 50 wt %; most preferably, 35 to 45 wt %), based on weight of the acrylate rich stage, of at least one $C_{6-22}$ alkyl (meth)acrylate selected from the group consisting of ethylhexyl (meth)acrylate, lauryl (meth) acrylate, stearyl (meth)acrylate and mixtures thereof. Most preferably, the acrylate rich stage comprises: 88 to 100 wt % (preferably, 94 to 99.49 wt %; more preferably, 97 to 99.23 wt %; still more preferably, 97.9 to 98.95 wt %; most preferably, 97.45 to 98.05 wt %), based on weight of the acrylate rich stage, of structural units of a monoethylenically unsaturated non-ionic, acrylate rich stage monomer; wherein the monoethylenically unsaturated non-ionic, acrylate rich stage monomer is selected from the group consisting of a mixture of (i) 40 to 75 wt % (more preferably, 50 to 70 wt %; most preferably, 55 to 65 wt %), based on weight of the acrylate rich stage, of at least one $C_{1-4}$ alkyl (meth)acrylate selected from the group consisting of butyl acrylate, butyl methacrylate isobutyl methacrylate, methyl methacrylate and mixtures thereof; and (ii) 25 to 60 wt % (more preferably, 30 to 50 wt %; most preferably, 35 to 45 wt %), based on weight of the acrylate rich stage, of at least one $C_{6-22}$ alkyl (meth)acrylate selected from the group consisting of ethylhexyl acrylate, ethylhexyl methacrylate and mixtures thereof.

Preferably, the acrylate rich stage comprises: 0 to 10 wt % (preferably, 0.5 to 5 wt %; more preferably, 0.75 to 2.5 wt %; still more preferably, 1 to 2 wt %; most preferably, 1.25 to 1.75 wt %), based on weight of the acrylate rich stage, of structural units of a monoethylenically unsaturated carboxylic acid, acrylate rich stage monomer. More preferably, the acrylate rich stage comprises: 0 to 10 wt % (preferably, 0.5 to 5 wt %; more preferably, 0.75 to 2.5 wt %; still more preferably, 1 to 2 wt %; most preferably, 1.25 to 1.75 wt %), based on weight of the acrylate rich stage, of structural units of a monoethylenically unsaturated carboxylic acid, acrylate rich stage monomer; wherein the monoethylenically unsaturated carboxylic acid, acrylate rich stage monomer is selected from the group consisting of (meth)acrylic acid, (meth)acryloxypropionic acid, itaconic acid, aconitic acid, maleic acid, maleic anhydride, fumaric acid, crotonic acid, citraconic acid, maleic anhydride, monomethyl maleate, monomethyl fumarate, monomethyl itaconate, other derivatives (such as corresponding anhydride, amides and esters) and mixtures thereof. Still more preferably, the acrylate rich stage comprises: 0 to 10 wt % (preferably, 0.5 to 5 wt %; more preferably, 0.75 to 2.5 wt %; still more preferably, 1 to 2 wt %; most preferably, 1.25 to 1.75 wt %), based on weight of the acrylate rich stage, of structural units of a monoethylenically unsaturated carboxylic acid, acrylate rich stage monomer; wherein the monoethylenically unsaturated carboxylic acid, acrylate rich stage monomer is selected from the group consisting of acrylic acid, methacrylic acid, itaconic acid, crotonic acid and mixtures thereof. Yet more preferably, the acrylate rich stage comprises: 0 to 10 wt % (preferably, 0.5 to 5 wt %; more preferably, 0.75 to 2.5 wt %; still more preferably, 1 to 2 wt %; most preferably, 1.25 to 1.75 wt %), based on weight of the acrylate rich stage, of structural units of a monoethylenically unsaturated carboxylic acid, acrylate rich stage monomer; wherein the monoethylenically unsaturated carboxylic acid, acrylate rich stage monomer is selected from the group consisting of at least one of acrylic acid and methacrylic acid. Most preferably, the acrylate rich stage comprises: 0 to 10 wt % (preferably, 0.5 to 5 wt %; more preferably, 0.75 to 2.5 wt %; still more preferably, 1 to 2 wt %; most preferably, 1.25 to 1.75 wt %), based on weight of the acrylate rich stage, of structural units of a monoethylenically unsaturated carboxylic acid, acrylate rich stage monomer; wherein the monoethylenically unsaturated carboxylic acid, acrylate rich stage monomer is methacrylic acid.

Preferably, the acrylate rich stage comprises: 0 to 2 wt % (preferably, 0.01 to 1 wt %; more preferably, 0.02 to 0.5 wt %; still more preferably, 0.05 to 0.1 wt %; most preferably, 0.07 to 0.08 wt %), based on weight of the acrylate rich stage, of structural units of a multiethylenically unsaturated, acrylate rich stage monomer having at least two ethylenically unsaturated groups per molecule. More preferably, the acrylate rich stage comprises: 0 to 2 wt % (preferably, 0.01 to 1 wt %; more preferably, 0.02 to 0.5 wt %; still more preferably, 0.05 to 0.1 wt %; most preferably, 0.07 to 0.08 wt %), based on weight of the acrylate rich stage, of structural units of a multiethylenically unsaturated, acrylate rich stage monomer having at least two ethylenically unsaturated groups per molecule; wherein the multiethylenically unsaturated monomer having at least two ethylenically unsaturated groups per molecule is selected from the group consisting of divinylaromatic compounds, di-(meth)acrylate esters, tri-(meth)acrylate esters, tetra-(methacrylate)esters, di-allyl ethers, tri-allyl ethers, tetra-allyl ethers, di-allyl esters, tri-allyl esters, tetra-allyl esters, allyl (meth)acrylate and mixtures thereof. Still more preferably, the acrylate rich stage comprises: 0 to 2 wt % (preferably, 0.01 to 1 wt %; more preferably, 0.02 to 0.5 wt %; still more preferably, 0.05 to 0.1 wt %; most preferably, 0.07 to 0.08 wt %), based on weight of the acrylate rich stage, of structural units of a multiethylenically unsaturated, acrylate rich stage monomer having at least two ethylenically unsaturated groups per molecule; wherein the multiethylenically unsaturated monomer having at least two ethylenically unsaturated groups per molecule is selected from the group consisting of divinylbenzene (DVB), trimethylolpropane diallyl ether, tetra-allyl pentaerythritol, triallyl pentaerythritol, diallyl pentaerythritol, diallyl phthalate, diallyl maleate, triallyl cyanurate, Bisphenol A diallyl ether, allyl sucroses, methylene bisacrylamide, trimethylolpropane triacrylate, allyl methacrylate (ALMA), ethylene glycol dimethacrylate (EGDMA), hexane-1,6-diol diacrylate (HDDA), butylene glycol dimethacrylate (BGDMA) and mixtures thereof. Yet more preferably, the acrylate rich stage comprises: 0 to 2 wt % (preferably, 0.01 to 1 wt %; more preferably, 0.02 to 0.5 wt %; still more preferably, 0.05 to 0.1 wt %; most preferably, 0.07 to 0.08 wt %), based on weight of the acrylate rich stage, of structural units of a multiethylenically unsaturated, acrylate rich stage monomer having at least two ethylenically unsaturated groups per molecule; wherein the multiethylenically unsaturated monomer having at least two ethylenically unsaturated groups per molecule is selected from the group consisting of DVB, ALMA, EGDMA, HDDA and BGDMA. Yet still more preferably, the acrylate rich stage comprises: 0 to 2 wt % (preferably, 0.01 to 1 wt %; more preferably, 0.02 to 0.5 wt %; still more preferably, 0.05 to 0.1 wt %; most preferably, 0.07 to 0.08 wt %), based on weight of the acrylate rich stage, of structural units of a multiethylenically unsaturated, acrylate rich stage monomer having at least two ethylenically unsaturated groups per molecule; wherein the multiethylenically unsaturated monomer having at least two ethylenically unsaturated groups per molecule includes ALMA. Most preferably, the acrylate rich stage comprises: 0 to 2 wt % (preferably, 0.01 to 1 wt %; more preferably, 0.02 to 0.5 wt %; still more preferably, 0.05 to 0.1 wt %; most preferably, 0.07 to 0.08 wt %), based on weight of the acrylate rich stage, of structural units of a multiethylenically unsaturated, acrylate rich stage monomer having at least two ethylenically unsaturated groups per molecule;

wherein the multiethylenically unsaturated monomer having at least two ethylenically unsaturated groups per molecule is ALMA.

Preferably, the multistage polymer, comprises an carbosiloxane rich stage. More preferably, the multistage polymer, comprises: 5 to 40 wt % (preferably, 10 to 35 wt %; more preferably, 15 to 30 wt %; most preferably, 18 to 25 wt %), based on weight of the multistage polymer, of a carbosiloxane rich stage. Most preferably, the multistage polymer, comprises: 5 to 40 wt % (preferably, 10 to 35 wt %; more preferably, 15 to 30 wt %; most preferably, 18 to 25 wt %), based on weight of the multistage polymer, of a carbosiloxane rich stage; wherein the carbosiloxane rich stage comprises: 0 to 90 wt % (preferably, 10 to 50 wt %; more preferably, 12.5 to 30 wt %; still more preferably, 15 to 25 wt %; most preferably, 19 to 21 wt %), based on weight of the carbosiloxane rich stage, of structural units of a vinyl monomer; and 10 to 100 wt % (preferably, 50 to 90 wt %; more preferably, 70 to 87.5 wt %; still more preferably, 75 to 85 wt %; most preferably, 79 to 81 wt %), based on weight of the carbosiloxane rich stage, of structural units of a carbosiloxane monomer of formula (I).

Preferably, the carbosiloxane rich stage comprises: 0 to 90 wt % (preferably, 10 to 50 wt %; more preferably, 12.5 to 30 wt %; still more preferably, 15 to 25 wt %; most preferably, 19 to 21 wt %), based on weight of the carbosiloxane rich stage, of structural units of a vinyl (A) monomer. More preferably, the carbosiloxane rich stage comprises: 0 to 90 wt % (preferably, 10 to 50 wt %; more preferably, 12.5 to 30 wt %; still more preferably, 15 to 25 wt %; most preferably, 19 to 21 wt %), based on weight of the carbosiloxane rich stage, of structural units of a vinyl (A) monomer; wherein the vinyl (A) monomer contains at least one radically polymerizable vinyl group per molecule. Still more preferably, the carbosiloxane rich stage comprises: 0 to 90 wt % (preferably, 10 to 50 wt %; more preferably, 12.5 to 30 wt %; still more preferably, 15 to 25 wt %; most preferably, 19 to 21 wt %), based on weight of the carbosiloxane rich stage, of structural units of a vinyl (A) monomer; wherein the vinyl (A) monomer is selected from the group consisting of $C_{1-3}$ alkyl acrylates (e.g., methyl acrylate, ethyl acrylate, n-propyl acrylate, isopropyl acrylate); $C_{1-3}$ alkyl methacrylates (e.g., methyl methacrylate, ethyl methacrylate, n-propyl methacrylate, isopropyl methacrylate); monoethylenically unsaturated carboxylic acids (e.g., (meth)acrylic acid, (meth)acryloxypropionic acid, itaconic acid, aconitic acid, maleic acid, maleic anhydride, fumaric acid, crotonic acid, citraconic acid, maleic anhydride, monomethyl maleate, monomethyl fumarate, monomethyl itaconate); $C_{4-20}$ alkyl acrylates (e.g., n-butyl acrylate, isobutyl acrylate, tert-butyl acrylate, n-hexyl acrylate, cyclohexyl acrylate, 2-ethylhexyl acrylate, octyl acrylate, lauryl acrylate, stearyl acrylate); $C_{4-20}$ alkyl methacrylates (e.g., n-butyl methacrylate, isobutyl methacrylate, tert-butyl methacrylate, n-hexyl methacrylate, cyclohexyl methacrylate, 2-ethylhexyl methacrylate, octyl methacrylate, lauryl methacrylate, stearyl methacrylate); aromatic vinyl monomers (e.g., styrene, vinyl toluene, benzyl acrylate, benzyl methacrylate, phenoxyethyl acrylate, phenoxyethyl methacrylate, vinyl pyrrolidone); and mixtures thereof. Yet more preferably, the carbosiloxane rich stage comprises: 0 to 90 wt % (preferably, 10 to 50 wt %; more preferably, 12.5 to 30 wt %; still more preferably, 15 to 25 wt %; most preferably, 19 to 21 wt %), based on weight of the carbosiloxane rich stage, of structural units of a vinyl (A) monomer; wherein the vinyl (A) monomer is selected from the group consisting of methyl acrylate, ethyl acrylate, n-propyl acrylate, isopropyl acrylate, methyl methacrylate, ethyl methacrylate, n-propyl methacrylate, isopropyl methacrylate, n-butyl acrylate, isobutyl acrylate, tert-butyl acrylate, n-hexyl acrylate, cyclohexyl acrylate, 2-ethylhexyl acrylate, n-butyl methacrylate, isobutyl methacrylate, tert-butyl methacrylate, n-hexyl methacrylate, 2-ethylhexyl methacrylate, methacrylic acid and mixtures thereof. Most preferably, the carbosiloxane rich stage comprises: 0 to 90 wt % (preferably, 10 to 50 wt %; more preferably, 12.5 to 30 wt %; still more preferably, 15 to 25 wt %; most preferably, 19 to 21 wt %), based on weight of the carbosiloxane rich stage, of structural units of a vinyl (A) monomer; wherein the vinyl (A) monomer includes methyl methacrylate and methacrylic acid.

Preferably, the carbosiloxane rich stage comprises: 10 to 100 wt % (preferably, 50 to 90 wt %; more preferably, 70 to 87.5 wt %; still more preferably, 75 to 85 wt %; most preferably, 79 to 81 wt %), based on weight of the carbosiloxane rich stage, of structural units of a carbosiloxane monomer of formula (I). More preferably, the carbosiloxane rich stage comprises: 10 to 100 wt % (preferably, 50 to 90 wt %; more preferably, 70 to 87.5 wt %; still more preferably, 75 to 85 wt %; most preferably, 79 to 81 wt %), based on weight of the carbosiloxane rich stage, of structural units of a carbosiloxane monomer of formula (I), wherein a is 0 to 3 (preferably, 0 to 2; most preferably, 1); wherein d is 0 or 1 (preferably, 0); wherein each $R^1$ is independently selected from the group consisting of a hydrogen, a $C_{1-10}$ alkyl group and an aryl group (preferably, a hydrogen and a $C_{1-10}$ alkyl group; more preferably, a hydrogen and a $C_{1-4}$ alkyl group; still more preferably, a hydrogen and a methyl group; most preferably, a methyl group); wherein each $R^2$ is independently selected from the group consisting of a hydrogen and a $C_{1-10}$ alkyl group (preferably, a hydrogen and a $C_{1-5}$ alkyl group; more preferably, a hydrogen and a $C_{1-4}$ alkyl group; still more preferably, a hydrogen and a methyl group; most preferably, a methyl group); wherein each $R^8$ is a —O—Si(CH$_3$)$_2$—O—Si(CH$_3$)$_3$ group; wherein Y is selected from the group consisting of formula (II), (III) and (IV) (preferably, (II) or (III); most preferably, (II)); wherein each $R^4$ and $R^6$ are independently selected from the group consisting of a hydrogen and a methyl group (preferably, a methyl group); wherein each $R^3$ and $R^5$ are independently a $C_{1-10}$ alkylene group (preferably, a $C_{1-7}$ alkylene group; more preferably, a $C_{2-6}$ alkylene group; still more preferably, a $C_{3-5}$ alkylene group; most preferably, a $C_3$ alkylene group); wherein each $R^7$ is independently a $C_{1-10}$ alkyl group; wherein b is 0 to 4 and wherein c is 0 or 1. Most preferably, the carbosiloxane rich stage comprises: 10 to 100 wt % (preferably, 50 to 90 wt %; more preferably, 70 to 87.5 wt %; still more preferably, 75 to 85 wt %; most preferably, 79 to 81 wt %), based on weight of the carbosiloxane rich stage, of structural units of a carbosiloxane monomer of formula (I), wherein a is 1; wherein d is 0; wherein each $R^1$ is a methyl group; wherein each $R^2$ is a methyl group; wherein Y is of formula (II); wherein each $R^3$ is a $C_{3-5}$ alkylene group; and wherein each $R^4$ is a methyl group.

Preferably, the polymer blend of the present invention comprises a silicone-grafted vinyl copolymer. More preferably, the polymer blend of the present invention, comprises 1 to 90 wt % (preferably, 10 to 85 wt %; more preferably, 20 to 80 wt %; most preferably, 25 to 75 wt %), based on weight solids of the polymer blend, of a silicone-grafted vinyl copolymer, wherein the silicone-grafted vinyl copolymer, comprises: 25 to 95 wt % (preferably, 30 to 70 wt %; more preferably, 40 to 60 wt %; still more preferably, 45 to 55 wt %; most preferably, 47.5 to 52.5 wt %), based on weight of the silicone-grafted vinyl copolymer, of structural units of a vinyl (B) monomer; and 5 to 75 wt % (preferably, 30 to 70 wt %; more preferably, 40 to 60 wt %; still more preferably, 45 to 55 wt %; most preferably, 47.5 to 52.5 wt %), based on weight of the silicone-grafted vinyl copolymer, of structural units of a carbosiloxane dendrimer of formula (V). Most preferably, the polymer blend of the present invention, comprises 1 to 90 wt % (preferably, 10 to 85 wt %; more preferably, 20 to 80 wt %; most preferably, 25 to 75 wt %), based on weight solids of the polymer blend, of a silicone-grafted vinyl copolymer; wherein the silicone-grafted vinyl copolymer comprises: 25 to 95 wt % (preferably, 30 to 70 wt %; more preferably, 40 to 60 wt %; still more preferably, 45 to 55 wt %; most preferably, 47.5 to 52.5 wt %), based on weight of the silicone-grafted vinyl copolymer, of structural units of a vinyl (B) monomer; and 5 to 75 wt % (preferably, 30 to 70 wt %; more preferably, 40 to 60 wt %; still more preferably, 45 to 55 wt %; most preferably, 47.5 to 52.5 wt %), based on weight of the silicone-grafted vinyl copolymer, of structural units of a carbosiloxane dendrimer of formula (V); wherein the silicone-grafted vinyl copolymer is an acrylates/polytrimethylsiloxymethacrylate copolymer.

Preferably, the silicone-grafted vinyl copolymer comprises 25 to 95 wt % (preferably, 30 to 70 wt %; more preferably, 40 to 60 wt %; still more preferably, 45 to 55 wt %; most preferably, 47.5 to 52.5 wt %), based on weight of the silicone-grafted vinyl copolymer, of structural units of a vinyl (B) monomer. More preferably, the silicone-grafted vinyl copolymer comprises 25 to 95 wt % (preferably, 30 to 70 wt %; more preferably, 40 to 60 wt %; still more preferably, 45 to 55 wt %; most preferably, 47.5 to 52.5 wt %), based on weight of the silicone-grafted vinyl copolymer, of structural units of a vinyl (B) monomer; wherein the vinyl (B) monomer contains at least one radically polymerizable vinyl group per molecule. Still more preferably, the silicone-grafted vinyl copolymer comprises 25 to 95 wt % (preferably, 30 to 70 wt %; more preferably, 40 to 60 wt %; still more preferably, 45 to 55 wt %; most preferably, 47.5 to 52.5 wt %), based on weight of the silicone-grafted vinyl copolymer, of structural units of a vinyl (B) monomer; wherein the vinyl (B) monomer is selected from the group consisting of $C_{1-3}$ alkyl acrylates (e.g., methyl acrylate, ethyl acrylate, n-propyl acrylate, isopropyl acrylate); $C_{1-3}$ alkyl methacrylates (e.g., methyl methacrylate, ethyl methacrylate, n-propyl methacrylate, isopropyl methacrylate); $C_{4-20}$ alkyl acrylates (e.g., n-butyl acrylate, isobutyl acrylate, tert-butyl acrylate, n-hexyl acrylate, cyclohexyl acrylate, 2-ethylhexyl acrylate, octyl acrylate, lauryl acrylate, stearyl acrylate); $C_{4-20}$ alkyl methacrylates (e.g., n-butyl methacrylate, isobutyl methacrylate, tert-butyl methacrylate, n-hexyl methacrylate, cyclohexyl methacrylate, 2-ethylhexyl methacrylate, octyl methacrylate, lauryl methacrylate, stearyl methacrylate); vinyl esters of lower aliphatic acids (e.g., vinyl acetate, vinyl propionate); vinyl esters of higher aliphatic acids (e.g., vinyl butyrate, vinyl caproate, vinyl-2-ethylhexanoate, vinyl laurate, vinyl stearate); aromatic vinyl monomers (e.g., styrene, vinyl toluene, benzyl acrylate, benzyl methacrylate, phenoxyethyl acrylate, phenoxyethyl methacrylate, vinyl pyrrolidone); amino functional vinyl monomers (e.g., dimethylaminoethyl acrylate, dimethylaminoethyl methacrylate, diethylaminoethyl acrylate, and diethylaminoethyl methacrylate); amide functional vinyl monomers (e.g., acrylamide, N-methylolacrylamide, N-methoxymethylacrylamide, isobutoxymethoxyacrylamide, N,N-dimethylacrylamide, methacrylamide, N-methylolmethacrylamide, N-methoxymethylmethacrylamide, obutoxymethoxymethacrylamide, N,N-dimethylmethacrylamide); hydroxyl-functional vinyl monomers (e.g., 2-hydroxyethyl acrylate, 2-hydroxybutyl acrylate, 2-hydroxypropyl acrylate, 2-hydroxyethyl methacrylate, 2-hydroxybutyl methacrylate, 2-hydroxypropyl methacrylate); fluorinated vinyl monomers (e.g., trifluoropropyl acrylate, perfluorobutylethyl acrylate, perfluorooctylethyl acrylate, trifluoropropyl methacrylate, perfluorobutylethyl methacrylate, perfluorooctylethyl methacrylate); epoxy-functional vinyl monomers (e.g., glycidyl acrylate, 3,4-epoxycyclohexylmethyl acrylate, glycidyl methacrylate, 3,4-epoxycyclohexylmethyl methacrylate); ether linkage containing vinyl monomers (e.g., tetrahydrofurfuryl acrylate, butoxyethyl acrylate, ethoxydiethylene glycol acrylate, polyethylene glycol acrylate, polypropylene glycol monoacrylate, hydroxybutyl vinyl ether, cetyl vinyl ether, 2-ethylhexyl vinyl ether, tetrahydrofurfuryl methacrylate, butoxyethyl methacrylate, ethoxydiethyleneglycol methacrylate, polyethylene glycol methacrylate, polypropyleneglycol monomethacrylate); alkoxysilanes that contain a radically polymerizable unsaturated group (e.g., $CH_2=CHCOOC_3H_6Si(OCH_3)_3$, $CH_2=C(CH_3)COOC_3H_6Si(OCH_3)_3$, $CH_2=C(CH_3)COOC_3H_6Si(CH_3)(OCH_3)_2$, $CH_2=C(CH_3)COOC_3H_6Si(CH_3)_2OCH_3$, $CH_2=C(CH_3)COOC_2H_4OC_3H_6Si(OCH_3)_3$, $CH_2=C(CH_3)COOC_{12}H_{24}Si(OCH_3)_3$, $CH_2=CHOC_3H_6Si(CH_3)(OC_2H_5)_2$, $CH_2=CHSi(OCH_3)_3$, $CH_2=CHSi(OC_2H_5)_3$, $CH_2=CHSi(C_4H_9)(OC_4H_9)_2$); unsaturated group-functionalized silicone compounds (e.g., branched or straight chain organopolysiloxane bearing an acryl or methacryl group at a single terminal; polydimethylsiloxane bearing a styryl group at a single terminal); butadiene; vinyl chloride; vinylidene chloride; acrylonitrile; methacrylonitrile; dibutyl fumarate; maleic anhydride, dodecylsuccinic anhydride; radically polymerizable unsaturated carboxylic acids (e.g., acrylic acid, methacrylic acid, itaconic acid, crotonic acid, fumaric acid, maleic acid, as well as their alkali metal salts, ammonium salts and organic amine salts); radically polymerizable unsaturated monomers containing a sulfonic acid residue (e.g., styrene sulfonic acid, as well as their alkali metal salts, ammonium salts and organic amine salts); quaternary ammonium salts that are derived from (meth)acrylic acid (e.g., 2-hydroxy-3-methacryloxypropyltrimethylammonium chloride); methacrylate esters of alcohols that contain a tertiary amine group (e.g., diethylamine ester of methacrylic acid, as well as the quaternary ammonium salts thereof); and mixtures thereof. Yet more preferably, the silicone-grafted vinyl copolymer comprises 25 to 95 wt % (preferably, 30 to 70 wt %; more preferably, 40 to 60 wt %; still more preferably, 45 to 55 wt %; most preferably, 47.5 to 52.5 wt %), based on weight of the silicone-grafted vinyl copolymer, of structural units of a vinyl (B) monomer; wherein the vinyl (B) monomer is selected from the group consisting of $C_{1-3}$ alkyl acrylates (e.g., methyl acrylate, ethyl acrylate, n-propyl acrylate, isopropyl acrylate); $C_{1-3}$ alkyl methacrylates (e.g., methyl methacrylate, ethyl methacrylate, n-propyl methacrylate, isopropyl methacrylate); $C_{4-20}$ alkyl acrylates (e.g., n-butyl acrylate, isobutyl acrylate, tert-butyl acrylate, n-hexyl acrylate, cyclohexyl acrylate, 2-ethylhexyl acrylate, octyl acrylate, lauryl acrylate, stearyl acrylate); $C_{4-20}$ alkyl methacrylates (e.g., n-butyl methacrylate, isobutyl methacrylate, tert-butyl methacrylate, n-hexyl methacrylate, cyclohexyl methacrylate, 2-ethylhexyl methacrylate, octyl methacrylate, lauryl methacrylate, stearyl methacrylate); aromatic vinyl monomers (e.g., styrene, vinyl toluene, benzyl acrylate, benzyl methacrylate, phenoxyethyl acrylate, phenoxyethyl methacrylate, vinyl pyrrolidone); and mixtures thereof. Yet still more preferably, the silicone-grafted vinyl copolymer comprises 25 to 95 wt % (preferably, 30 to 70 wt %; more preferably, 40 to 60 wt %; still more preferably, 45 to 55 wt %; most preferably, 47.5 to 52.5 wt %), based on weight of the silicone-grafted vinyl copolymer, of structural units of a vinyl (B) monomer; wherein the vinyl (B) monomer is selected from the group consisting of methyl acrylate, ethyl acrylate, n-propyl acrylate, isopropyl acrylate, methyl methacrylate, ethyl methacrylate, n-propyl methacrylate, isopropyl methacrylate, n-butyl acrylate, isobutyl acrylate, tert-butyl acrylate, n-hexyl acrylate, cyclohexyl acrylate, 2-ethylhexyl acrylate, n-butyl methacrylate, isobutyl methacrylate, tert-butyl methacrylate, n-hexyl methacrylate, 2-ethylhexyl methacrylate, styrene and mixtures thereof. Most preferably, the silicone-grafted vinyl copolymer comprises 25 to 95 wt % (preferably, 30 to 70 wt %; more preferably, 40 to 60 wt %; still more preferably, 45 to 55 wt %; most preferably, 47.5 to 52.5 wt %), based on weight of the silicone-grafted vinyl copolymer, of structural units of vinyl (B) monomer; wherein the vinyl (B) monomer includes methyl methacrylate and butyl acrylate.

Preferably, the silicone-grafted vinyl copolymer comprises 5 to 75 wt % (preferably, 30 to 70 wt %; more preferably, 40 to 60 wt %; still more preferably, 45 to 55 wt %; most preferably, 47.5 to 52.5 wt %), based on weight of the silicone-grafted vinyl copolymer, of structural units of a carbosiloxane dendrimer of formula (V). More preferably, the silicone-grafted vinyl copolymer comprises 5 to 75 wt % (preferably, 30 to 70 wt %; more preferably, 40 to 60 wt %; still more preferably, 45 to 55 wt %; most preferably, 47.5 to 52.5 wt %), based on weight of the silicone-grafted vinyl copolymer, of structural units of a carbosiloxane dendrimer of formula (V); wherein each $R^9$ is independently selected from the group consisting of a $C_{1-10}$ alkyl group and an aryl group (preferably, wherein each $R^9$ is a methyl group); wherein each X is a silylalkyl group of formula (VI); wherein $R^{10}$ is a $C_{2-10}$ alkylene group (preferably, wherein $R^{10}$ is a $C_{2-5}$ alkylene group; more preferably, wherein $R^{10}$ is a $C_{2-4}$ alkylene group; most preferably, wherein $R^{10}$ is a $C_2$ alkylene group); wherein each $R^{11}$ is independently a $C_{1-10}$ alkyl group (preferably, wherein each $R^{11}$ is independently a $C_{1-5}$ alkyl group; more preferably, wherein each $R^{11}$ is independently a $C_{1-4}$ alkyl group; most preferably, wherein each $R^{11}$ is a methyl group); wherein each Z is independently selected from the group consisting of a hydrogen, a $C_{1-10}$ alkyl group, an aryl group and a silylalkyl group of formula (VI) (preferably, wherein each Z is a methyl group); wherein e is 0 to 3 (preferably, wherein e is 0); wherein A is selected from the group consisting of formula (VII), (VIII) and (IX) (preferably, wherein A is of formula (VII)); wherein each $R^{12}$ and $R^{14}$ are independently a hydrogen or a methyl group (preferably; wherein each $R^{12}$ and $R^{14}$ are a methyl group); wherein each $R^{13}$ and $R^{16}$ are independently a $C_{1-10}$ alkylene group (preferably, wherein each $R^{13}$ and $R^{16}$ are independently a $C_{2-5}$ alkylene group; more preferably, wherein each $R^{13}$ and $R^{16}$ are independently a $C_{2-4}$ alkylene group; most preferably, wherein each $R^{13}$ and $R^{16}$ are independently a $C_3$ alkylene group); wherein each $R^{15}$ is independently a $C_{1-10}$ alkyl group (preferably, wherein each $R^{15}$ is independently a $C_{1-5}$ alkyl group; more preferably, wherein each $R^{15}$ is independently a $C_{1-4}$ alkyl group; most preferably, wherein each $R^{15}$ is a methyl group); wherein f is 0 to 4; wherein g is 0 or 1. Still more preferably, the silicone-grafted vinyl copolymer of the present invention comprises 5 to 75 wt % (preferably, 30 to 70 wt %; more preferably, 40 to 60 wt %; still more preferably, 45 to 55 wt %; most preferably, 47.5 to 52.5 wt %), based on weight of the silicone-grafted vinyl copolymer, of structural units of a carbosiloxane dendrimer of formula (V); wherein A is selected from the group consisting of acryloxymethyl, 3-acryloxypropyl, methacryloxymethyl, 3-methyacryloxypropyl, 4-vinylphenyl, 3-vinylphenyl, 4-(2-propenyl)phenyl, 3-(2-propenyl)phenyl, 2-(4-vinylphenyl)ethyl and 2-(3-vinylphenyl)ethyl. Yet more preferably, the silicone-grafted vinyl copolymer of the present invention comprises 5 to 75 wt % (preferably, 30 to 70 wt %; more preferably, 40 to 60 wt %; still more preferably, 45 to 55 wt %; most preferably, 47.5 to 52.5 wt %), based on weight of the silicone-grafted vinyl copolymer, of structural units of a carbosiloxane dendrimer of formula (V); wherein A is selected from the group consisting of acryloxymethyl, 3-acryloxypropyl, methacryloxymethyl and 3-methyacryloxypropyl. Still yet more preferably, the silicone-grafted vinyl copolymer of the present invention comprises 5 to 75 wt % (preferably, 30 to 70 wt %; more preferably, 40 to 60 wt %; still more preferably, 45 to 55 wt %; most preferably, 47.5 to 52.5 wt %), based on weight of the silicone-grafted vinyl copolymer, of structural units of a carbosiloxane dendrimer of formula (V); wherein A is selected from the group consisting of 3-acryloxypropyl and 3-methyacryloxypropyl. Most preferably, the silicone-grafted vinyl copolymer of the present invention comprises 5 to 75 wt % (preferably, 30 to 70 wt %; more preferably, 40 to 60 wt %; still more preferably, 45 to 55 wt %; most preferably, 47.5 to 52.5 wt %), based on weight of the silicone-grafted vinyl copolymer, of structural units of a carbosiloxane dendrimer of formula (V); wherein each $R^9$ is a methyl group; wherein $R^{19}$ is a $C_2$ alkylene group; wherein e is 0; wherein each Z is a methyl group; wherein A is of formula (VII); wherein $R^{12}$ is a methyl group and wherein $R^{13}$ is a $C_3$ alkylene group.

Preferably, the personal care formulation of the present invention comprises a polymer blend of the present invention. More preferably, the personal care formulation of the present invention comprises: 0.1 to 10 wt % (preferably, 0.5 to 7.5 wt %; more preferably, 1 to 7 wt %; still more preferably, 3 to 5 wt %; most preferably, 3.5 to 4.5 wt %) of a polymer blend of the present invention. Most preferably, the personal care formulation of the present invention comprises: 0.1 to 10 wt % (preferably, 0.5 to 7.5 wt %; more preferably, 1 to 7 wt %; still more preferably, 3 to 5 wt %; most preferably, 3.5 to 4.5 wt %) of a polymer blend of the present invention dispersed in a cosmetically acceptable carrier.

Preferably, the personal care formulation of the present invention, comprise a cosmetically acceptable carrier. More preferably, the personal care formulation of the present invention, comprises: 30 to 92 wt % (preferably, 35 to 92 wt %; more preferably, 40 to 80 wt %) of a cosmetically acceptable carrier. Most preferably, the personal care formulation of the present invention, comprises 30 to 92 wt % (preferably, 35 to 92 wt %; more preferably, 40 to 80 wt %) of a cosmetically acceptable carrier; wherein the polymer blend of the present invention is dispersed in the cosmetically acceptable carrier.

Preferably, the personal care formulation of the present invention, comprises 30 to 92 wt % (preferably, 35 to 92 wt %; more preferably, 40 to 80 wt %) of a cosmetically acceptable carrier; wherein the cosmetically acceptable carrier is selected to be capable of evaporating upon application of the personal care formulation to mammalian skin or hair (preferably, human skin).

Preferably, the personal care formulation of the present invention, comprises 30 to 92 wt % (preferably, 35 to 92 wt %; more preferably, 40 to 80 wt %) of a cosmetically acceptable carrier; wherein the cosmetically acceptable is selected from the group consisting of water (e.g., deionized, distilled water); emulsions (e.g., oil-in-water emulsion, water-in-oil emulsion); alcohols (e.g., $C_{1-4}$ straight or branched chain alcohols such as ethyl alcohol, propyl alcohol, isopropyl alcohol, butyl alcohol); glycols (e.g., ethylene glycol, propylene glycol, butylene glycol, pentylene glycol, hexylene glycol, dipropylene glycol, ethoxydiglycol); glycerin; butyl cellosolve and mixtures thereof. More preferably, the personal care formulation of the present invention, comprises 30 to 92 wt % (preferably, 35 to 92 wt %; more preferably, 40 to 80 wt %) of a cosmetically acceptable carrier; wherein the cosmetically acceptable carrier includes water (preferably, at least one of deionized water and distilled water; more preferably, deionized, distilled water).

Preferably, the personal care formulation of the present invention, further comprises a suncare active. Preferably, the personal care formulation of the present invention comprises 0.1 to 70 wt % (preferably, 5 to 65 wt %; more preferably, 7.5 to 60 wt %; most preferably, 10 to 55 wt %) of a suncare active. More preferably, the personal care formulation of the present invention comprises 0.1 to 70 wt % (preferably, 5 to 65 wt %; more preferably, 7.5 to 60 wt %; most preferably, 10 to 55 wt %) of a suncare active; wherein the suncare active is a UV radiation absorbing agent. Still more preferably, the personal care formulation of the present invention, comprises 0.1 to 70 wt % (preferably, 5 to 65 wt %; more preferably, 7.5 to 60 wt %; most preferably, 10 to 55 wt %) of a suncare active, wherein the suncare active is a UV radiation absorbing agent selected from the group consisting of physical blockers (e.g., red petrolatum, titanium dioxide, zinc oxide) and chemical absorbers (e.g., 1-(4-methoxyphenol)-3-(4-tert-butylphenyl)propane-1,3-dione (INCI: Butyl Methoxydibenzoylmethane); 2-hydroxy-4-methoxybenzophenone (INCI: Benzophenone-3); dioxybenzone; sulisobenzone; menthyl anthranilate; para-aminobenzoic acid; amyl paradimethylaminobenzoic acid; octyl para-dimethylaminobenzoate; ethyl 4-bis (hydroxypropyl) para-aminobenzoate; polyethylene glycol (PEG-25) para-aminobenzoate; ethyl 4-bis (hydroxypropyl) aminobenzoate; diethanolamine para-methyoxycinnamate; 2-ethoxyethyl para-methoxycinnamate; ethylhexyl para-methoxycinnamate; octyl para-methoxycinnamate; isoamyl para-methoxycinnamate; 2-ethylhexyl-2-cyano-3,3-diphenylacrylate; 2-ethylhexyl-2-cyano-3,3-diphenyl-2-propenoate (INCI: octocrylene); 2-ethylhexyl-2-hydroxybenzoate (INCI: Ethylhexyl Salicylate); homomenthyl salicylate; glyceryl aminobenzoate; triethanolamine salicylate; digalloyl trioleate; lawsone with dihydroxyacetone; 2-phenylbenzimidazole-5-sulfonic acid; 4-methylbenzylidine camphor; avobenzone; triazines; benzotriazoles; vinyl group-containing amides; cinnamic acid amides; sulfonated benzimidazoles); 3,3,5-trimethylcyclohexyl 2-hydroxybenzoate (INCI: Homosalate). Yet more preferably, the personal care formulation of the present invention, comprises 0.1 to 70 wt % (preferably, 5 to 65 wt %; more preferably, 7.5 to 60 wt %; most preferably, 10 to 55 wt %) of a suncare active, wherein the suncare active is a UV radiation absorbing agent comprises a mixture of UV radiation absorbing agents. Yet still more preferably, the personal care formulation of the present invention, comprises 0.1 to 70 wt % (preferably, 5 to 65 wt %; more preferably, 7.5 to 60 wt %; most preferably, 10 to 55 wt %) of a suncare active, wherein the suncare active is a UV radiation absorbing agent is a mixture of UV absorbing agents including at least one of 1-(4-methoxyphenol)-3-(4-tert-butylphenyl)propane-1,3-dione; 2-ethylhexyl-2-hydroxybenzoate; 2-ethyhexyl-2-cyano-3,3-diphenyl-2-propenoate; 2-hydroxy-4-methoxybenzophenone and 3,3,5-trimethylcyclohexyl 2-hydroxybenzoate. Most preferably, the personal care formulation of the present invention, comprises 0.1 to 70 wt % (preferably, 5 to 65 wt %; more preferably, 7.5 to 60 wt %; most preferably, 10 to 55 wt %) of a suncare active, wherein the suncare active is a UV radiation absorbing agent is a mixture of UV absorbing agents including 1-(4-methoxyphenol)-3-(4-tert-butylphenyl)propane-1,3-dione; 2-ethylhexyl 2-hydroxybenzoate; 2-ethylhexyl-2-cyano-3,3-diphenyl-2-propenoate and 2-hydroxy-4-methoxybenzophenone.

Preferably, the personal care formulation of the present invention, further comprises 0 to 20 wt % (preferably, 0.5 to 15 wt %; more preferably, 1 to 10 wt %; most preferably, 2 to 5 wt %) of a SPF booster. Preferably, the SPF booster is not an active ingredient, but is designed to enhance the effectiveness of the sunscreen actives present in the formulation. Suitable SPF boosters include, but are not limited to, styrene/acrylates copolymer, sodium bentonite, highly purified white sodium bentonite, montmorillonite, hydrogel, or any combinations thereof. A particularly preferred styrene/acrylates copolymer for use in the suncare formulation of the present invention is sold under the trade name SunSpheres® by The Dow Chemical Company.

Preferably, the personal care formulation of the present invention, optionally, further comprises an optional additive. More preferably, the personal care formulation of the present invention, further comprises an optional additive, wherein the optional additive is selected from the group consisting of water proofing agents, emollients, preservatives, antioxidants, fragrances, deodorants, antiperspirant actives, skin coolants, humectants, rheology modifiers, aesthetic modifiers, Vitamins, skin protectants, oils, emulsifiers, surfactants, pearlizers, consistency factors, thickeners, super fatting agents, stabilizers, polymers, silicone oils, fats, waxes, lecithins, phospholipids, fillers, pigments, colorants, light management powders and particles, moisturizers, cleansers, hair treatment actives, anti-dandruff agents, skin care actives and mixtures thereof.

Preferably, the personal care formulation of the present invention, optionally, further comprises a color ingredient. More preferably, the personal care formulation of the present invention, optionally, further comprises a color ingredient; wherein the color ingredient is selected from the group consisting of inorganic pigments, organic pigments, aqueous pigment dispersions and mixtures thereof. Still more preferably, the personal care formulation of the present invention, optionally, further comprises a color ingredient; wherein the color ingredient is selected from the group consisting of Ext. D&C Yellow No. 2, Ext. D & C Violet No. 2, FD&C Red No. 4, FD&C Red No. 40, FD&C Yellow No. 5, FD&C Yellow No. 6, FD&C Green No. 3, FD&C Blue No. 1, D&C Yellow No. 7, D&C Yellow No. 8, D&C Yellow No. 10, D&C Yellow No. 11, D&C Violet No. 2, D&C Red No. 6, D&C Red No. 7, D&C Red No. 17, D&C Red No. 21, D&C Red No. 22, D&C Red No. 27, D&C Red No. 28, D&C Red No. 30, D&C Red No. 31, D&C Red No. 34, D&C Red No. 33, D&C Red No. 36, D&C Green No. 5, D&C Green No. 6, D&C Green No. 8, D&C Blue No. 4, D&C Orange No. 4, D&C Orange No. 5, D&C Orange No. 10, D&C Orange No. 11, D&C Brown No. 1, Aluminum powder, Annatto, Bismuth citrate, Bismuth Oxychloride, Bronze powder, Caramel, Carmine, β-Carotene, Chromium hydroxide green, Chromium oxide green, Copper chlorophyllin, Copper powder, Dihydroxyacetone, Ferric Ammonium ferrocyanide, Ferric ferrocyanide, Guanine, Iron oxide, Manganese Violet, Mica, Silver, Titanium Dioxide, Ultramarine, Zinc Oxide and mixtures thereof. Still more preferably, the color cosmetic formulation of the present invention comprises a color ingredient; wherein the color ingredient includes at least one iron oxide. Most preferably, the personal care formulation of the present invention, optionally, further comprises a color ingredient; wherein the color ingredient includes a mixture of iron oxides.

Preferably, the personal care formulation of the present invention, further comprises a color ingredient, wherein the color ingredient is a pigment. More preferably, the personal care formulation of the present invention, further comprises a color ingredient, wherein the color ingredient is a pigment and wherein the pigment has a surface treatment. Still more preferably, the personal care formulation of the present invention, further comprises a color ingredient; wherein the color ingredient is a pigment; wherein the pigment has a surface treatment and wherein the surface treatment is formed through treatment of the pigment with a surface treatment agent selected from the group consisting of an alkyl silane, a halogenated phosphonate, a halogenated organosilane or a combination thereof. Most preferably, the personal care formulation of the present invention, further comprises a color ingredient; wherein the color ingredient is a pigment; wherein the pigment has a surface treatment and wherein the surface treatment is formed through treatment of the pigment with a surface treatment agent selected from the group consisting of sodium perfluorohexylethylphosphonate, triethoxy caprylylsilane, perfluorooctyltriethoxysilane and mixtures thereof.

Preferably, the personal care formulation of the present invention has a pH of 4 to 9. More preferably, the personal care formulation of the present invention has a pH of 4.5 to 8.5. Still more preferably, the personal care formulation of the present invention has a pH of 5.0 to 8.0. Most preferably, the personal care formulation of the present invention has a pH of 5.5 to 7.5.

Preferably, the personal care formulation of the present invention is provided a product form selected from the group consisting of a cream, an aqueous solution, an oil, an ointment, a paste, a gel, a lotion, a milk, a foam, a suspension, a stick and a spray.

The personal care formulations of the present invention are useful for the protection of skin or hair. Preferably, the personal care formulations of the present invention are useful for protecting skin from UV damage from exposure to the sun. The personal care formulations of the present invention also preferably provide moisturization to the skin, prevention and treatment of dry skin, protection of sensitive skin, improvement of skin tone and texture, masking imperfections, and inhibition of trans-epidermal water loss. Thus, the present invention provides personal care formulations that can be used in a method for protecting skin from UV damage comprising topically administering the personal care formulation to the skin.

The multistage polymer can be prepared by conventional polymerization techniques, such as, for example, by emulsion polymerization. Preferably, the multistage polymer of the present invention is an emulsion polymer.

Some embodiments of the present invention will now be described in detail in the following Examples.

The monomer abbreviations used in the Examples are described in TABLE 1.

TABLE 1

| Abbreviation | Monomer |
| --- | --- |
| BA | Butyl Acrylate |
| BMA | Butyl Methacrylate |

TABLE 1-continued

| Abbreviation | Monomer |
| --- | --- |
| IBMA | Isobutyl Methacrylate |
| EHA | 2-Ethylhexyl Acrylate |
| EHMA | 2-Ethylhexyl Methacrylate |
| MMA | Methyl Methacrylate |
| MAA | Methacrylic Acid |
| ALMA | Allyl Methacrylate |
| MD'M-ALMA | (structure) |
| M'DM-IPMA | (structure) |

Comparative Example CS1: Single Stage Polymer

A 1-liter round-bottom flask equipped with an overhead stirrer, thermocouple, condenser and inlets for the addition of monomer and initiators was charged with deionized water (150.0 g), sodium dodecyl sulfonate surfactant (3.3 g of a 23% DS-4) and sodium carbonate (1.1 g). The flask contents were then stirred and heated at 85° C. A monomer emulsion was prepared by charging deionized water (81.1 g) and sodium dodecyl sulfonate surfactant (3.1 g of 23% DS-4) to a container and set to stir. After the surfactant was incorporated into the water, butyl acrylate (BA) (50 g), ethylhexyl acrylate (EHA) (100 g), methyl methacrylate (MMA) (96.3 g), methacrylic acid (MAA) (3.8 g) and allyl methacrylate (ALMA) (0.2 g) were added slowly to the stirring mixture in the container. A cofeed catalyst solution was also prepared by charging sodium persulfate (0.25 g) and deionized water (22 g) in another container. When the flask contents reached a temperature of 85° C., 10 g of the above prepared monomer emulsion was charged to the flask, followed with a deionized water rinse (10 g) water rinse, followed by an initiator solution of sodium persulfate (0.9 g) in deionized water (5.7 g). After initial polymerization and at 85° C., a monomer emulsion cofeed to the flask of the above prepared monomer emulsion was begun at a rate of 1.97 g/min for 15 minutes and then at a rate of 3.93 g/min. for the next 75 minutes. Simultaneously, with the monomer emulsion cofeed the catalyst cofeed was begun at a rate of 0.24 g/min for 92 minutes. At the completion of the cofeeds, the flask contents were chased to reduce the amount of residual monomers to provide the product single stage polymer.

Comparative Example CS2: Dendritic Silicone-Grafted Vinyl Copolymer

A flask equipped with an overhead stirrer, thermocouple, condenser and inlets for the addition of monomer and initiators was charged with carbosiloxane dendrimer (150 parts) with the following structure

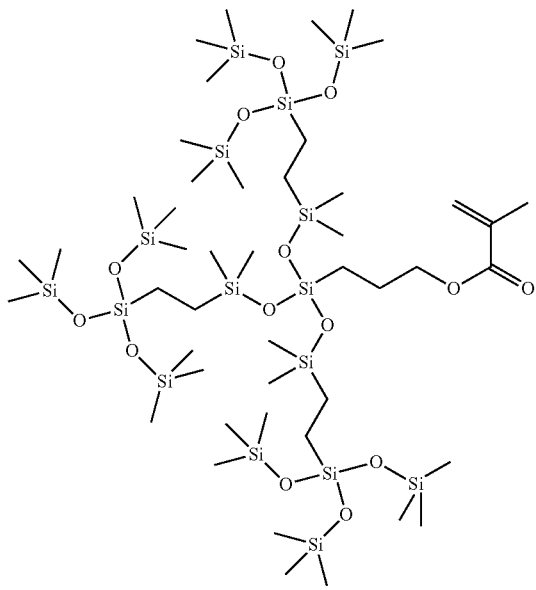 [SMILES: C=C(C)C(=O)OCCC[Si](O[Si](C)(C)CC[Si](O[Si](C)(C)C)(O[Si](C)(C)C)O[Si](C)(C)C)(O[Si](C)(C)CC[Si](O[Si](C)(C)C)(O[Si](C)(C)C)O[Si](C)(C)C)O[Si](C)(C)CC[Si](O[Si](C)(C)C)(O[Si](C)(C)C)O[Si](C)(C)C]

methyl methacrylate (MMA) (99 parts), n-butyl methacrylate (BMA) (51 parts) and 2-phenoxyethanol (9 parts). To the flask contents was then was added laureth-1 phosphate (7 parts), sodium hydroxide solution (4 parts, 20%) and deionized water (676 parts). The flask contents were then emulsified and dispersed using a homogenizer. The flask contents were then heated to 80° C., under a nitrogen. Upon reaching temperature, potassium persulfate (2.2 parts) was added to the flask contents while maintaining the temperature controller at 80° C. After three hours after the potassium persulfate addition, 2,2'-azobis[N-(2-carboxyethyl)-2-methylpropionamidine] tetrahydrate (2.2 parts) was added to the flask contents while maintaining the temperature controller at 80° C. The flask contents were allowed to stir for three additional hours while maintaining the temperature controller at 80° C., to provide the product dendritic silicone-grafted vinyl copolymer.

Example S1: Multistage Polymer

A 2-liter round-bottom flask (equipped with an overhead stirrer, thermocouple, condenser and inlets for the addition of monomer and initiators) was charged with deionized water (252.0 g), 50% CAVASOL™ W7 MTL (cyclodextrin from Wacker Fine Chemicals) (5.3 g), 23% DS-4 surfactant (5.3 g) (A-16-22 from Stepan) and sodium carbonate (1.8 g). The flask contents were stirred and heated to 85° C.

An acrylate rich monomer emulsion was prepared by charging deionized water (103.8 g) and 23% DS-4 surfactant (4.0 g) to a first container and set to stir. Once the surfactant was incorporated into the water the following monomers were added slowly to the first container with continued stirring: BA (64 g), EHA (128.0 g), MMA (123.2 g), methyl acrylic acid MAA (4.8 g) and ALMA (0.24 g).

A carbosiloxane rich monomer emulsion was prepared by charging deionized water (26.0 g) and 23% DS-4 surfactant (1.0 g) to a second container and set to stir. Once the surfactant was incorporated into the water the following monomers were added slowly to the second container with continued stirring: MD'M-ALMA (64 g), MMA (14.8 g) and MAA (1.2 g). The carboxiloxane rich monomer emulsion was further emulsified using the homogenization at 10 K rpm for 10 min.

A cofeed catalyst solution was prepared containing sodium persulfate (0.8 g) and deionized water (35.2 g).

A cofeed buffer solution was prepared containing sodium carbonate (0.8 g) and deionized water (35.2 g).

At a reaction set point temperature of 85° C., 12.8 g of the acrylate rich monomer emulsion from the first container along with a deionized water rinse (16.0 g) was charged to the flask contents. An initiator solution of sodium persulfate (1.8 g) in deionized water (12.0 g) was then added to the flask contents. After the initial polymerization, the remainder of the acrylate rich monomer emulsion in the first container was cofeed to the flask contents at a rate of 3.08 g/min. for 15 minutes and then at 6.15 g/min for 60 minutes. Simultaneously with the acrylate rich monomer emulsion cofeed, the cofeed catalyst solution and the cofeed buffer solution were added to the reactor contents at a rate of 0.39 g/min. for 92 minutes.

Following the addition of the acrylate rich monomer emulsion, the carbosiloxane rich monomer emulsion in the second container was added to the reactor contents at a rate of 7.23 g/min for 15 minutes. After completion of the various feeds, the contents of the flask were chased to reduce the amount of residual monomers, providing the product multistage polymer.

Example S2: Multistage Polymer

The multistage polymer of Example S2 was prepared in the same fashion as the multistage polymer of Example S1 except that the carbosiloxane rich monomer emulsion was added to the flask contents as a shot. After addition, the reaction mixture was held steady with stirring at 85° C. for 20 minutes. At the end of the hold time, catalyst and buffer co-feed was restarted. At the completion of catalyst cofeed, the flask contents were chased to reduce the amount of residual monomers, providing the product multistage polymer.

Examples S3-S19: Multistage Polymer

Multistage polymers were prepared substantially as described in Example S1 the appropriate changes being made reflecting the total wt % of the acrylate rich stage and the carbosiloxane rich stage in the respective multistage polymers of Examples S3-S19 with the acrylate rich stage monomers and the carbosiloxane rich stage monomers in the respective stages as noted in TABLE 2.

TABLE 2

Multistage polymer

| | Acrylate rich stage | | | | | | | | | Carbosiloxane rich stage | | | | |
| | Total | Monomer (wt %) | | | | | | | | Total | Monomer (wt %) | | | |
| Ex. | wt % | BA | BMA | IBMA | EHA | EHMA | MMA | MAA | ALMA | wt % | MAA | MMA | MD'M-ALMA | MD'M-IPMA |
|---|---|---|---|---|---|---|---|---|---|---|---|---|---|---|
| S1 | 80 | 20 | — | — | 40 | — | 38.5 | 1.5 | 0.075 | 20 | 1.5 | 18.5 | 80 | — |
| S2 | 80 | 20 | — | — | 40 | — | 38.5 | 1.5 | 0.075 | 20 | 1.5 | 18.5 | 80 | — |
| S3 | 90 | 20 | — | — | 40 | — | 38.5 | 1.5 | 0.075 | 10 | 1.5 | 18.5 | 80 | — |
| S4 | 70 | 20 | — | — | 40 | — | 38.5 | 1.5 | 0.075 | 30 | 1.5 | 18.5 | 80 | — |
| S5 | 80 | 20 | — | — | 40 | — | 38.5 | 1.5 | 0.075 | 20 | 1.5 | 33.5 | 65 | — |
| S6 | 80 | — | — | — | 40 | — | 58.5 | 1.5 | 0.075 | 20 | 1.5 | 18.5 | 80 | — |
| S7 | 80 | 20 | — | — | — | — | 78.5 | 1.5 | 0.075 | 20 | 1.5 | 18.5 | 80 | — |
| S8 | 80 | 20 | — | — | 40 | — | 38.5 | 1.5 | 0.075 | 20 | 1.5 | 18.5 | — | 80 |
| S9 | 80 | — | 20 | — | 40 | — | 38.5 | 1.5 | 0.075 | 20 | 1.5 | 18.5 | 80 | — |
| S10 | 80 | — | — | 20 | 40 | — | 38.5 | 1.5 | 0.075 | 20 | 1.5 | 18.5 | 80 | — |
| S11 | 70 | — | 20 | — | 40 | — | 38.5 | 1.5 | 0.075 | 30 | 1.5 | 18.5 | 80 | — |
| S12 | 70 | — | — | 20 | 40 | — | 38.5 | 1.5 | 0.075 | 30 | 1.5 | 18.5 | 80 | — |
| S13 | 80 | 20 | — | — | — | 40 | 38.5 | 1.5 | 0.075 | 20 | 1.5 | 18.5 | 80 | — |
| S14 | 70 | 20 | — | — | — | 40 | 38.5 | 1.5 | 0.075 | 30 | 1.5 | 18.5 | 80 | — |
| S15 | 70 | 50 | 23.5 | — | — | — | 25 | 1.5 | 0.075 | 30 | 1.5 | 18.5 | 80 | — |
| S16 | 70 | 40 | 33.5 | — | — | — | 25 | 1.5 | 0.075 | 30 | 1.5 | 18.5 | 80 | — |
| S17 | 80 | 40 | 33.5 | — | — | — | 25 | 1.5 | 0.075 | 20 | 1.5 | 18.5 | 80 | — |
| S18 | 80 | 30 | 43.5 | — | — | — | 25 | 1.5 | 0.075 | 20 | 1.5 | 18.5 | 80 | — |
| S19 | 80 | 20 | 53.5 | — | — | — | 25 | 1.5 | 0.075 | 20 | 1.5 | 18.5 | 80 | — |

Polymer Properties

The product multistage polymers prepared according to Comparative Example CS1 and Examples S1-S19 were analyzed for percent solids, pH, mean particle size (using Brookhaven Instruments BI-90 particle size analyzer) and glass transition temperature, Tg, as measured using a TA instruments model 2920 Differential Scanning calorimeter (DSC). The results are provided in TABLE 3.

TABLE 3

| Example | % solids | pH | PS (nm) | Tg (° C.) |
|---|---|---|---|---|
| CS1 | 41.04 | 5.87 | 117.1 | −10 |
| S1 | 43.38 | 5.60 | 145.2 | −7.6 |
| S2 | 39.36 | 5.77 | 201.5 | −12.3 |
| S3 | 39.41 | 5.87 | 122.1 | −7.5 |
| S4 | 38.90 | 5.74 | 130.4 | −8.9 |
| S5 | 38.06 | 5.74 | 139.0 | −11.6 |
| S6 | 39.37 | 5.77 | 126.5 | 28.5 |
| S7 | 40.65 | 5.72 | 153.0 | 77.4 |
| S8 | 38.52 | 5.63 | 148.9 | −11.4 |
| S9 | 37.62 | 5.37 | 138.9 | 7.2 |
| S10 | 39.71 | 5.60 | 137.8 | 15.3 |
| S11 | 39.08 | 5.62 | 136.1 | 5.8 |
| S12 | 38.44 | 5.56 | 128.9 | 15.3 |
| S13 | 37.65 | 5.56 | 130.4 | 24.2 |
| S14 | 39.26 | 5.52 | 128.2 | 25.7 |
| S15 | 46.78 | 5.40 | 145.0 | −6.2 |
| S16 | 47.01 | 5.40 | 149.4 | 4.4 |
| S17 | 45.10 | 5.70 | 150.5 | 2.7 |
| S18 | 47.18 | — | 150.4 | 12.8 |
| S19 | 46.36 | — | 146.2 | 25.6 |

Example S20: Silicone-Grafted Vinyl Copolymer

A flask equipped with an overhead stirrer, thermocouple, condenser and inlets for the addition of monomer and initiators was charged with carbosiloxane dendrimer (150 parts) with the following structure

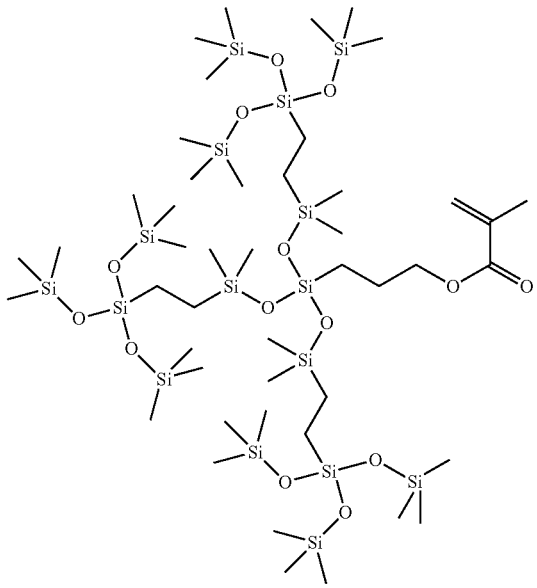 [SMILES: C=C(C)C(=O)OCCC[Si](O[Si](C)(C)CC[Si](O[Si](C)(C)C)(O[Si](C)(C)C)O[Si](C)(C)C)(O[Si](C)(C)CC[Si](O[Si](C)(C)C)(O[Si](C)(C)C)O[Si](C)(C)C)O[Si](C)(C)CC[Si](O[Si](C)(C)C)(O[Si](C)(C)C)O[Si](C)(C)C]

methyl methacrylate (MMA) (99 parts), n-butyl methacrylate (BMA) (51 parts) and 2-phenoxyethanol (9 parts). To the flask contents was then was added laureth-1 phosphate (7 parts), sodium hydroxide solution (4 parts, 20%) and deionized water (676 parts). The flask contents were then emulsified and dispersed using a homogenizer. The flask contents were then heated to 80° C., under a nitrogen. Upon reaching temperature, potassium persulfate (2.2 parts) was added to the flask contents while maintaining the temperature controller at 80° C. After three hours after the potassium persulfate addition, 2,2'-azobis[N-(2-carboxyethyl)-2-methylpropionamidine] tetrahydrate (2.2 parts) was added to the flask contents while maintaining the temperature controller at 80° C. The flask contents were allowed to stir for three additional hours while maintaining the temperature controller at 80° C., to provide the product silicone-grafted vinyl copolymer.

Formulation Examples G1 and G2: Generic Suncare Formulations

Generic suncare personal care formulations were prepared having the generic formulations according to Formulation Examples G1 and G2 noted in TABLE 4. The carbomer and some deionized water were added to a flask and mixed until the carbomer was hydrated before adding the remainder of the Phase I ingredients. The flask contents were then heated at 75° C. with mixing. The Phase II ingredients were combined in a separate container while being heated at 75° C. with mixing until dissolved. The Phase II ingredients were then added to the flask contents with mixing until uniform. The Phase III ingredients were then added to the flask contents with mixing until uniform. The flask contents were then removed from the heating source and cooled. When the flask contents cooled below 60° C., the Phase IV ingredients were added to the flask contents with mixing until uniform. When the flask contents cooled to below 40° C., the Phase V ingredients were added to the flask contents with continued mixing until the flask contents reached ambient room temperature. The flask contents were then pH adjusted to a pH of 5.5 to 7.5, as necessary.

In-Vitro SPF Measurements

The suncare formulations prepared according to Comparative Examples C1-C4 and Examples 1-6 were each allowed to settle for one week before in-vitro SPF measurements. The in-vitro SPF performance of each of the suncare formulations was then tested in triplicate using an in-vitro technique according to the following protocol.

The substrate used for the in-vitro SPF measurements was a rough PMMA substrate (6 μm-HD6 available from Schonberg GMBH & Co. KG). The suncare formulations to be tested were each applied to three separate rough PMMA substrates using an RDS #7 wire draw down bar to provide a uniform layer of the suncare formulation over the surface of the PMMA substrate at a rate of 1.2 to 1.3 mg/cm². Each deposited layer of suncare formulation was allowed to dry for fifteen (20) minutes under ambient conditions in the laboratory. The UV absorption of each dried layer of suncare formulation between 290 nm and 400 nm was then measured at six (6) separate points using a Labsphere UV-2000S Spectrometer. The in-vitro SPF value for each suncare formulation prepared according to Comparative Examples C1-C4 and Examples 1-6 was then calculated based on the results of the UV absorption measurements. The average from the triplicate samples of each suncare formulation prepared according to Comparative Examples C1-C4 and Examples 1-6 is reported in TABLE 5.

TABLE 4

| | | Generic Formulations | |
| --- | --- | --- | --- |
| Phase | Ingredient INCI name | Form. Ex. G1 Parts by weight (pbW) | Form. Ex. G2 Parts by weight (pbW) |
| | Deionized water | remainder to 100 | remainder to 100 |
| I | Carbomer[1] | 0.20 | 0.20 |
| I | Disodium EDTA[2] | 0.10 | 0.10 |
| I | Propylene Glycol | 2.00 | 2.00 |
| II | Avobenzone | 3.00 | 3.00 |
| II | Oxybenzone | 6.00 | 6.00 |
| II | Octyl Salicylate | 5.00 | 5.00 |
| II | Octocrylene | 10.00 | 10.00 |
| II | Hydrogenated Polydecene[3] | 7.00 | 7.00 |
| II | $C_{12-15}$ Alkyl Benzoate[4] | 5.00 | 5.00 |
| II | PEG 40 Stearate[5] | 1.00 | 1.00 |
| II | Glyceryl Stearate[6] | 1.00 | 1.00 |
| II | Cetearyl Alcohol, Cetereth-20[7] | 1.00 | 1.00 |
| III | Triethanolamine, 99% | 0.35 | 0.35 |
| IV | Polymer or polymer blend (on solids basis) | 1.00 | 3.00 |
| V | Preservative | 1.00 | 1.00 |

[1]Available from Rita under the tradename Acritamer 980.
[2]Available from The Dow Chemical Company under the tradenamer Versene NA.
[3]Available from Rita under the tradename Ritadecene 20.
[4]Available from Rita under the tradename Ritamollient TN.
[5]Available from Rita under the tradename Ritox 52.
[6]Available from Rita under the tradename Rita GMS.
[7]Available from Protameen under the tradename Procol CS-20-D.

Comparative Examples C1-C4 and Examples 1-6: Suncare Formulations

The suncare formulations of (a) Comparative Examples C1-C2 and Examples 1-3 and (b) Comparative Examples C3-C4 and Examples 4-6 were prepared according to Formulation Examples G1 and G2, respectively with the test polymer or polymer blend as noted in TABLE 5.

Water Resistance (In-Vitro SPF Retention)

The test substrates from the original in-vitro SPF measurements discussed above with applied formulations prepared according to Comparative Examples C1-C4 and Examples 1-6 were then each immersed in a controlled temperature water bath (30° C.) with a propeller agitation speed of 300 rpm for two hours. The substrates were then removed from the water bath and left to dry under ambient laboratory conditions for 20-30 minutes after which the in-vitro SPFs for each suncare formulation was measured and compared to its original in-vitro SPF measurement and the two hour SPF retention was calculated as reported in TABLE 5.

TABLE 5

| Formulation Example | Polymer Example | Polymer/Polymer Blend in wt % solids | | in-vitro SPF | |
|---|---|---|---|---|---|
| | | Ex. S17 | Ex. S20 | SPF | Retention (%) |
| C1 | G1 | 100 | 0 | 336 | 58 |
| C2 | G1 | 0 | 100 | 236 | 36 |
| C3 | G2 | 100 | 0 | 396 | 58 |
| C4 | G2 | 0 | 100 | 257 | 43 |
| 1 | G1 | 50 | 50 | 322 | 82 |
| 2 | G1 | 25 | 75 | 344 | 51 |
| 3 | G1 | 75 | 25 | 353 | 61 |
| 4 | G2 | 50 | 50 | 380 | 86 |
| 5 | G2 | 25 | 75 | 401 | 81 |
| 6 | G2 | 75 | 25 | 392 | 65 |

We claim:
1. A polymer blend, comprising:
(A) a multistage polymer, comprising:
  (a) an acrylate rich stage comprising:
    88 to 100 wt %, based on weight of the acrylate rich stage, of structural units of a monoethylenically unsaturated non-ionic, acrylate rich stage monomer, wherein the monoethylenically unsaturated non-ionic, acrylate rich stage monomer is selected from the group consisting of $C_{1-22}$ alkyl (meth)acrylates and mixtures thereof;
    0 to 10 wt %, based on weight of the acrylate rich stage, of structural units of a monoethylenically unsaturated carboxylic acid, acrylate rich stage monomer; and
    0 to 2 wt %, based on weight of the acrylate rich stage, of structural units of a multiethylenically unsaturated, acrylate rich stage monomer having at least two ethylenically unsaturated groups per molecule; and
  (b) a carbosiloxane rich stage, comprising:
    0 to 90 wt %, based on weight of the carbosiloxane rich stage, of structural units of a vinyl (A) monomer; and
    10 to 100 wt %, based on weight of the carbosiloxane rich stage, of structural units of a carbosiloxane monomer of formula (I)

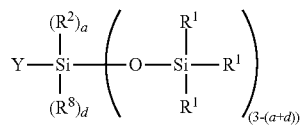

(I)

wherein a is 0 to 3; wherein d is 0 or 1; wherein each R1 is independently selected from the group consisting of a hydrogen, a $C_{1-10}$ alkyl group and an aryl group; wherein each $R^2$ is independently selected from the group consisting of a hydrogen and a $C_{1-10}$ alkyl group; wherein each $R^8$ is a —O—Si(CH$_3$)$_2$—O—Si(CH$_3$)$_3$ group; wherein Y is selected from the group consisting of formula (II), (III) and (IV)

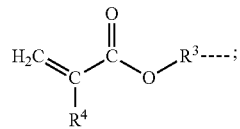

(II)

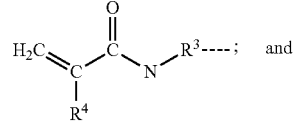

(III)

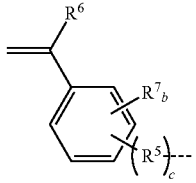

(IV)

wherein each $R^4$ and $R^6$ are independently selected from the group consisting of a hydrogen and a methyl group; wherein each $R^3$ and $R^5$ are independently a $C_{1-10}$ alkylene group; wherein each $R^7$ is independently a $C_{1-10}$ alkyl group; wherein b is 0 to 4 and wherein c is 0 or 1; and (B) a silicone-grafted vinyl copolymer, wherein the silicone-grafted vinyl copolymer, comprises:
  25 to 95 wt %, based on weight of the silicone-grafted vinyl copolymer, of structural units of a vinyl (B) monomer; and
  5 to 75 wt %, based on weight of the silicone-grafted vinyl copolymer, of structural units of a carbosiloxane dendrimer of formula (V)

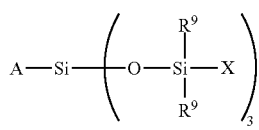

(V)

wherein each $R^9$ is independently selected from the group consisting of a $C_{1-10}$ alkyl group and an aryl group; wherein each X is a silylalkyl group of formula (VI)

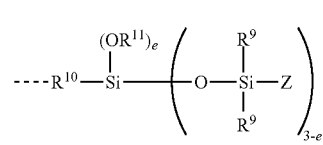

(VI)

wherein $R^{10}$ is a $C_{2-10}$ alkylene group; wherein each $R^{11}$ is independently a $C_{1-10}$ alkyl group; wherein each Z is independently selected from the group consisting of a hydrogen, a $C_{1-10}$ alkyl group, an aryl group and a silylalkyl group of formula (VI); wherein e is 0 to 3; wherein A is selected from the group consisting of formula (VII), (VIII) and (IX)

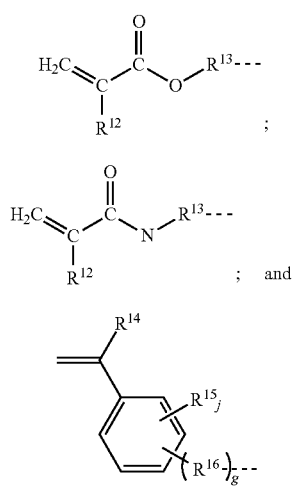

$$\underset{R^{12}}{\overset{H_2C}{=}}\overset{O}{\underset{}{\overset{\|}{C}}}-O-R^{13}--- \qquad (VII)$$

$$\underset{R^{12}}{\overset{H_2C}{=}}\overset{O}{\underset{}{\overset{\|}{C}}}-N-R^{13}--- \qquad (VIII)$$

; and (IX)

wherein each $R^{12}$ and $R^{14}$ are independently a hydrogen or a methyl group; wherein each $R^{13}$ and $R^{16}$ are independently a $C_{1-10}$ alkylene group; wherein each $R^{15}$ is independently a $C_{1-10}$ alkyl group; wherein f is 0 to 4 and wherein g is 0 or 1.

2. A personal care formulation, comprising:
the polymer blend of claim 1 dispersed in a cosmetically acceptable carrier.

3. The personal care formulation of claim 2,
wherein the monoethylenically unsaturated non-ionic, acrylate rich stage monomer is selected from the group consisting of a mixture of (i) 40 to 75 wt % of a $C_{1-4}$ alkyl (meth)acrylate and (ii) 25 to 60 wt % of a $C_{6-22}$ alkyl (meth)acrylate selected from the group consisting of ethylhexyl (meth)acrylate, lauryl (meth)acrylate, stearyl (meth)acrylate, cetyl-eicosyl (meth)acrylate, behenyl (meth)acrylate and mixtures thereof;
wherein the monoethylenically unsaturated carboxylic acid, acrylate rich stage monomer is selected from the group consisting of acrylic acid, methacrylic acid, itaconic acid, crotonic acid and mixtures thereof;
wherein the multiethylenically unsaturated, acrylate rich stage monomer having at least two ethylenically unsaturated groups per molecule is selected from the group consisting of divinylaromatic compounds, di-(meth)acrylate esters, tri-(meth)acrylate esters, tetra-(methacrylate) esters, di-allyl ethers, tri-allyl ethers, tetra-allyl ethers, di-allyl esters, tri-allyl esters, tetra-allyl esters, allyl (meth)acrylate and mixtures thereof;
wherein the vinyl (A) monomer is selected from the group consisting of a mixture of methacrylic acid and methyl methacrylate;
wherein a is 1; wherein d is 0; wherein each $R^1$ is a methyl group; wherein each $R^2$ is a methyl group; wherein Y is of formula (II); wherein each $R^3$ is a $C_{3-5}$ alkylene group; and wherein each $R^4$ is a methyl group; and
wherein the vinyl (B) monomer is selected from the group consisting of $C_{1-3}$ alky (meth)acrylates; $C_{4-20}$ alkyl (meth)acrylates; vinyl esters of lower aliphatic acids; vinyl esters of higher aliphatic acids; aromatic vinyl monomers; amino functional vinyl monomers; amide functional vinyl monomers; hydroxyl-functional vinyl monomers; fluorinated vinyl monomers; epoxy-functional vinyl monomers; ether linkage containing vinyl monomers; alkoxysilanes that contain a radically polymerizable unsaturated group; unsaturated group-functionalized silicone compounds; butadiene; vinyl chloride; vinylidene chloride; acrylonitrile; methacrylonitrile; dibutyl fumarate; maleic anhydride, dodecylsuccinic anhydride; radically polymerizable unsaturated carboxylic acids; radically polymerizable unsaturated monomers containing a sulfonic acid residue; quaternary ammonium salts that are derived from (meth)acrylic acid; methacrylate esters of alcohols that contain a tertiary amine group and mixtures thereof;
and wherein the carbosiloxane dendrimer is of formula (V), wherein each $R^9$ is a methyl group; wherein $R^{10}$ is a $C_2$ alkylene group; wherein e is 0; wherein each Z is a methyl group; wherein A is of formula (VII); wherein $R^{12}$ is a methyl group and wherein $R^{13}$ is a $C_3$ alkylene group.

4. The personal care formulation of claim 3, further comprising a suncare active.

5. The personal care formulation of claim 4, having
30 to 92 wt % of the cosmetically acceptable carrier;
0.1 to 10 wt %, on a solids basis, of the polymer blend; and
0.1 to 70 wt % of the suncare active.

6. The personal care formulation of claim 5, wherein the cosmetically acceptable carrier includes water.

7. The personal care formulation of claim 6, wherein the suncare active is an UV radiation absorbing agent is selected from the group consisting of physical blockers and chemical absorbers.

8. The personal care formulation of claim 4, wherein the suncare active is an UV radiation absorbing agent selected from the group consisting of red petrolatum; titanium dioxide; zinc oxide; 1-(4-methoxyphenol)-3-(4-tert-butylphenyl) propane-1,3-dione; 2-hydroxy-4-methoxybenzophenone; dioxybenzone; sulisobenzone; menthyl anthranilate; para-aminobenzoic acid; amyl paradimethylaminobenzoic acid; octyl para-dimethylaminobenzoate; ethyl 4-bis (hydroxypropyl) para-aminobenzoate; polyethylene glycol (PEG-25) para-aminobenzoate; ethyl 4-bis (hydroxypropyl) aminobenzoate; diethanolamine para-methyoxycinnamate; 2-ethoxyethyl para-methoxycinnamate; ethylhexyl para-methoxycinnamate; octyl para-methoxycinnamate; isoamyl para-methoxycinnamate; 2-ethylhexyl-2-cyano-3,3-diphenyl-acrylate; 2-ethylhexyl-2-cyano-3,3-diphenyl-2-propenoate; 2-ethylhexyl-2-hydroxybenzoate; homomenthyl salicylate; glyceryl aminobenzoate; triethanolamine salicylate; digalloyl trioleate; lawsone with dihydroxyacetone; 2-phenylbenzimidazole-5-sulfonic acid; 4-methylbenzylidine camphor; avobenzone; triazines; benzotriazoles; vinyl group-containing amides; cinnamic acid amides; sulfonated benzimidazoles); 3,3,5-trimethylcyclohexyl 2-hydroxybenzoate and mixtures thereof.

9. The personal care formulation of claim 8, wherein the suncare active is an UV radiation absorbing agent, wherein the UV radiation absorbing agent is a mixture of UV absorbing agents including 1-(4-methoxyphenol)-3-(4-tert-butylphenyl) propane-1,3-dione; 2-ethylhexyl 2-hydroxybenzoate; 2-ethyhexyl-2-cyano-3,3-diphenyl-2-propenoate and 2-hydroxy-4-methoxybenzophenone; and wherein $R^3$ is a $C_3$ alkylene group.

10. The personal care formulation of claim 9, further comprising an optional additive selected from the group consisting of water proofing agents, emollients, preservatives, antioxidants, fragrances, deodorants, antiperspirant actives, skin coolants, humectants, rheology modifiers, aesthetic modifiers, Vitamins, skin protectants, oils, emulsifiers, surfactants, pearlizers, consistency factors, thickeners, super fatting agents, stabilizers, polymers, silicone oils, fats, waxes, lecithins, phospholipids, fillers, pigments, colorants, light management powders and particles, moisturizers, cleansers, hair treatment actives, anti-dandruff agents, skin care actives and mixtures thereof.

* * * * *